US009931181B2

(12) United States Patent
Allen et al.

(10) Patent No.: US 9,931,181 B2
(45) Date of Patent: Apr. 3, 2018

(54) FIXED HYBRID DENTAL ATTACHMENT ASSEMBLY AND METHODS OF USE

(71) Applicant: ZEST IP HOLDINGS, LLC, Escondido, CA (US)

(72) Inventors: Richard Robert Allen, Oceanside, CA (US); Christopher Michael Gervais, San Marcos, CA (US); James Irwin Johnson, Temecula, CA (US)

(73) Assignee: ZEST IP HOLDINGS, LLC, Escondido, CA (US)

( * ) Notice: Subject to any disclaimer, the term of this patent is extended or adjusted under 35 U.S.C. 154(b) by 0 days.

(21) Appl. No.: 15/009,713

(22) Filed: Jan. 28, 2016

(65) Prior Publication Data
US 2016/0143710 A1 May 26, 2016

Related U.S. Application Data

(63) Continuation-in-part of application No. 14/806,616, filed on Jul. 22, 2015, now Pat. No. 9,827,074.
(Continued)

(51) Int. Cl.
*A61C 8/00* (2006.01)
*A61C 3/16* (2006.01)
*A61C 13/20* (2006.01)

(52) U.S. Cl.
CPC ............ *A61C 8/0053* (2013.01); *A61C 3/168* (2013.01); *A61C 8/006* (2013.01); *A61C 8/0062* (2013.01); *A61C 8/0068* (2013.01); *A61C 13/20* (2013.01)

(58) Field of Classification Search
CPC ....... A61C 8/005; A61C 8/001; A61C 8/0075; A61C 8/008; A61C 8/0053; A61C 8/0086; A61C 8/0057; A61C 8/0059
See application file for complete search history.

(56) References Cited

U.S. PATENT DOCUMENTS

| 711,324 A | 10/1902 | Lacy |
| 3,514,858 A | 6/1970 | Silverman |

(Continued)

FOREIGN PATENT DOCUMENTS

| EP | 501940 A1 | 9/1992 |
| EP | 1621156 A1 | 2/2006 |

(Continued)

OTHER PUBLICATIONS

International Search Report and Written Opinion for PCTUS2016060845, dated Feb. 16, 2017, 16 pages.
(Continued)

*Primary Examiner* — Nicholas Lucchesi
*Assistant Examiner* — Shannel Wright
(74) *Attorney, Agent, or Firm* — Procopio, Cory, Hargreaves & Savitch, LLP; Katherine Proctor; Noel C Gillespie

(57) ABSTRACT

A frictionally-retained detachable dental attachment assembly or anchor device is designed to attach a dental appliance with a tooth root or implant. The assembly includes a denture attachment housing for securing in the dental appliance, an abutment attached with a tooth root or implant, and a compressible retention member with a first end in fixed attachment with the cap and a second end in snap engagement with the abutment via a frictionally-retained ball secured within a cavity of the abutment. The retention member is formed using a compressible material to allow the ball to compress and the retention member to flex while inserting the ball into the cavity. Additional friction-retained and fixed attachment configurations of the dental anchor device are provided, along with methods of securing a dental appliance in a subject's mouth by means of the friction-retained and fixed attachment dental anchor devices.

8 Claims, 27 Drawing Sheets

Related U.S. Application Data

(60) Provisional application No. 62/028,314, filed on Jul. 23, 2014, provisional application No. 62/027,780, filed on Jul. 22, 2014.

(56) References Cited

U.S. PATENT DOCUMENTS

| | | | |
|---|---|---|---|
| 3,732,621 A | 5/1973 | Bostrom | |
| 3,787,975 A | 1/1974 | Zuest | |
| 3,990,150 A | 11/1976 | Giovannini | |
| 3,991,472 A | 11/1976 | Lukesch | |
| 4,158,256 A | 6/1979 | Wiland et al. | |
| 4,290,755 A | 9/1981 | Scott | |
| 4,362,509 A | 12/1982 | Sulc | |
| 4,431,416 A | 2/1984 | Niznick et al. | |
| 4,475,891 A | 10/1984 | Hader | |
| 4,488,874 A * | 12/1984 | Soifer | A61C 8/0048 433/173 |
| 4,488,875 A | 12/1984 | Niznick et al. | |
| 4,518,357 A | 5/1985 | Brinkmann et al. | |
| 4,540,367 A | 9/1985 | Sulc | |
| 4,547,156 A | 10/1985 | Hader | |
| 4,568,285 A | 2/1986 | Chiaramonte et al. | |
| 4,626,213 A | 12/1986 | Shiner et al. | |
| 4,645,453 A | 2/1987 | Niznick et al. | |
| 4,657,510 A | 4/1987 | Gittleman et al. | |
| 4,738,623 A | 4/1988 | Driskell et al. | |
| 4,780,080 A | 10/1988 | Haris et al. | |
| 4,793,808 A | 12/1988 | Kirsch | |
| 4,832,601 A | 5/1989 | Linden et al. | |
| 4,854,872 A | 8/1989 | Detsch | |
| 4,907,969 A | 3/1990 | Ward | |
| 4,932,868 A | 6/1990 | Linkow et al. | |
| 4,934,935 A | 6/1990 | Edwards et al. | |
| 4,957,438 A | 9/1990 | Bax | |
| 4,988,297 A | 1/1991 | Lazzara et al. | |
| 5,030,095 A | 7/1991 | Niznick et al. | |
| 5,049,072 A | 9/1991 | Lueschen | |
| 5,071,350 A * | 12/1991 | Niznick | A61C 8/005 433/173 |
| 5,073,110 A * | 12/1991 | Barbone | A61C 8/0001 433/173 |
| 5,092,770 A | 3/1992 | Zakula | |
| 5,120,222 A | 6/1992 | Sulc | |
| 5,133,662 A | 7/1992 | Metcalfe | |
| 5,145,372 A * | 9/1992 | Daftary | A61C 8/005 433/173 |
| 5,178,539 A | 1/1993 | Peltier et al. | |
| 5,194,000 A | 3/1993 | Dury | |
| 5,195,891 A | 3/1993 | Sulc et al. | |
| 5,211,561 A | 5/1993 | Graub | |
| 5,302,125 A * | 4/1994 | Kownacki | A61C 8/0048 433/172 |
| 5,413,480 A | 5/1995 | Musikant et al. | |
| 5,417,570 A | 5/1995 | Zuest et al. | |
| 5,480,304 A | 1/1996 | Nardi et al. | |
| 5,520,540 A | 5/1996 | Nardi et al. | |
| 5,527,182 A | 6/1996 | Willoughby | |
| 5,556,280 A | 9/1996 | Pelak | |
| 5,564,924 A | 10/1996 | Kwan et al. | |
| 5,599,185 A | 2/1997 | Greenberg | |
| 5,630,717 A | 5/1997 | Zuest | |
| 5,636,989 A | 6/1997 | Somborac et al. | |
| 5,639,239 A | 6/1997 | Earle | |
| 5,662,475 A | 9/1997 | Mena et al. | |
| 5,678,997 A | 10/1997 | De Buck | |
| 5,839,898 A | 11/1998 | Fernandes et al. | |
| 5,888,218 A | 3/1999 | Folsom | |
| 5,890,902 A | 4/1999 | Sapian | |
| 5,954,505 A | 9/1999 | Ford | |
| 5,993,212 A | 11/1999 | Shiner | |
| 6,030,219 A | 2/2000 | Zuest et al. | |
| 6,287,115 B1 * | 9/2001 | Lustig | A61C 8/0022 433/172 |
| 6,299,447 B1 | 10/2001 | Zuest et al. | |
| 6,302,693 B1 | 10/2001 | Mena | |
| 6,332,777 B1 | 12/2001 | Sutter | |
| 6,500,003 B2 | 12/2002 | Nichinonni | |
| 6,716,030 B1 | 4/2004 | Bulard et al. | |
| 6,843,653 B2 | 1/2005 | Carlton | |
| 6,981,871 B2 | 1/2006 | Mullaly et al. | |
| 7,214,063 B2 * | 5/2007 | Cohen | A61C 8/005 433/173 |
| 7,704,076 B2 | 4/2010 | Mullaly et al. | |
| 7,959,439 B2 | 6/2011 | Bulloch et al. | |
| 8,128,403 B2 | 3/2012 | Karmon | |
| D666,298 S | 8/2012 | Sibhatu et al. | |
| 9,456,881 B1 | 10/2016 | Niznick | |
| 2002/0177103 A1 | 11/2002 | Pelak | |
| 2003/0224329 A1 | 12/2003 | Carlton | |
| 2003/0224331 A1 | 12/2003 | Kumar et al. | |
| 2005/0019730 A1 | 1/2005 | Gittleman | |
| 2006/0024644 A1 | 2/2006 | Cohen | |
| 2006/0275735 A1 | 12/2006 | Bulard et al. | |
| 2008/0153063 A1 | 6/2008 | Mullaly et al. | |
| 2008/0241790 A1 | 10/2008 | Gittleman | |
| 2009/0155745 A1 | 6/2009 | Laux | |
| 2009/0202962 A1 | 8/2009 | Xam-Mar Mangrane | |
| 2009/0246734 A1 | 10/2009 | Bar Shalom | |
| 2010/0055645 A1 | 3/2010 | Mullaly et al. | |
| 2010/0105005 A1 * | 4/2010 | Bulloch | A61C 8/0048 433/173 |
| 2010/0129773 A1 | 5/2010 | Chen | |
| 2010/0159420 A1 | 6/2010 | Mullaly et al. | |
| 2010/0232869 A1 | 9/2010 | Ditzler et al. | |
| 2010/0330536 A1 | 12/2010 | Mullaly | |
| 2012/0045737 A1 | 2/2012 | Ang | |
| 2012/0214128 A1 | 8/2012 | Collins et al. | |
| 2012/0288827 A1 | 11/2012 | McBride et al. | |
| 2012/0295223 A1 * | 11/2012 | Robb | A61C 8/008 433/173 |
| 2012/0315599 A1 | 12/2012 | Mullaly | |
| 2013/0209957 A1 | 8/2013 | Sanchez et al. | |
| 2014/0162211 A1 | 6/2014 | Mullaly et al. | |
| 2014/0162212 A1 | 6/2014 | Mullaly et al. | |
| 2014/0178838 A1 * | 6/2014 | McBride | A61C 8/0053 433/173 |
| 2015/0335401 A1 * | 11/2015 | Robichaud | A61C 8/0062 433/173 |

FOREIGN PATENT DOCUMENTS

| | | | |
|---|---|---|---|
| EP | 2647347 A1 * | 10/2013 | A61C 8/0053 |
| WO | 0028914 A2 | 5/2000 | |
| WO | 2008040134 A1 | 4/2008 | |
| WO | 2009156601 A2 | 12/2009 | |
| WO | 2010048558 A2 | 4/2010 | |
| WO | 2014082744 A1 | 6/2014 | |

OTHER PUBLICATIONS

Langer, et al., "Tooth-Supported Telescopic Prostheses in Comprised Dentitions: A clinical report" The Journal of Prosthetic Dentistry, 84 (2); 129-132 (2000).

International Search Report and Written Opinion for PCT/US2015041634, dated Oct. 16, 2015, 5 pages.

* cited by examiner

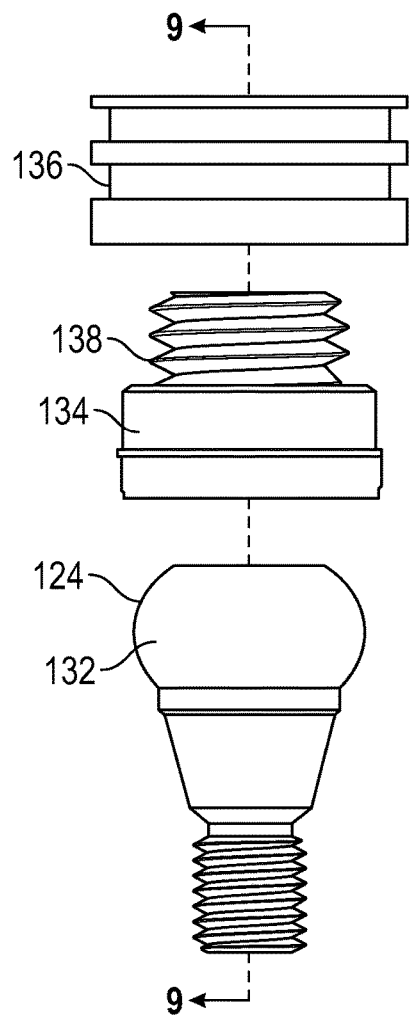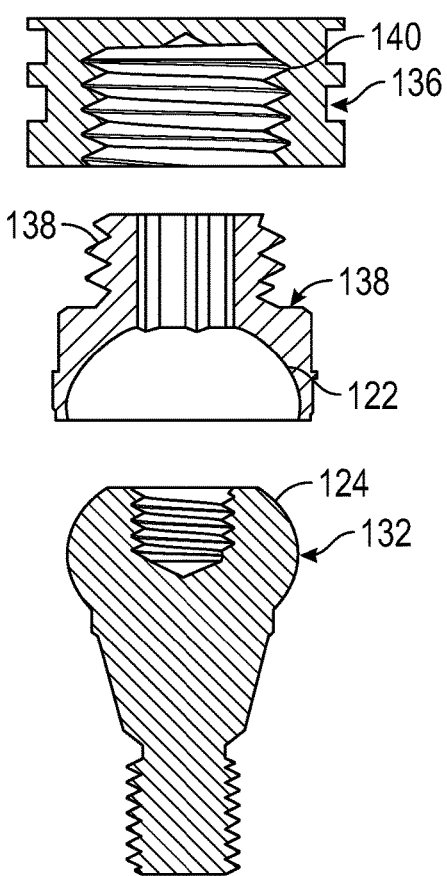
FIG. 8
FIG. 9

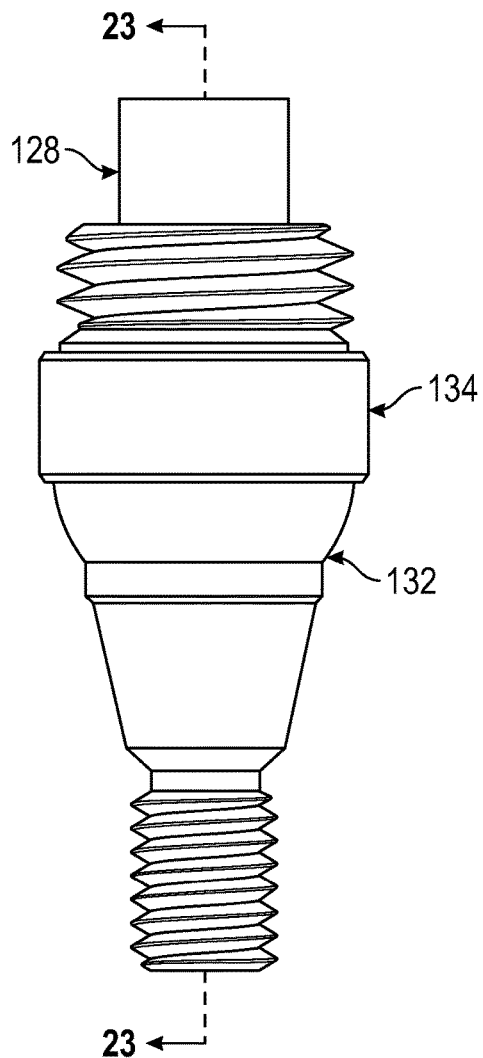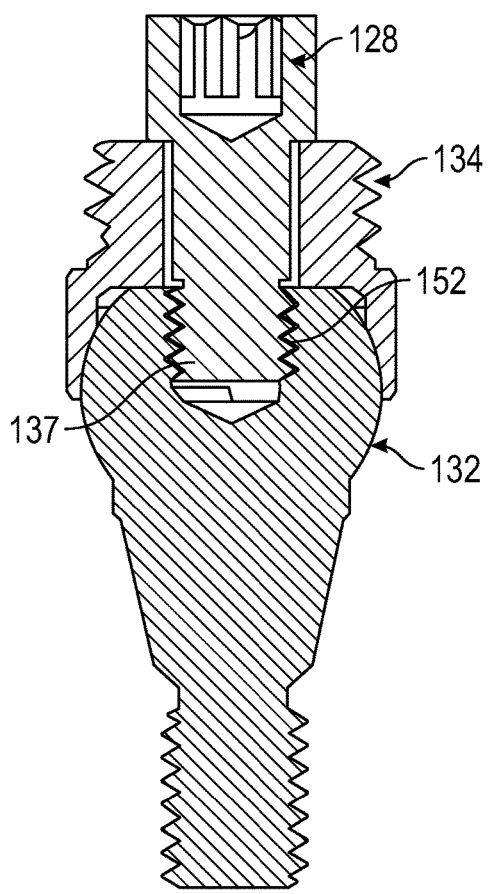
FIG. 22
FIG. 23

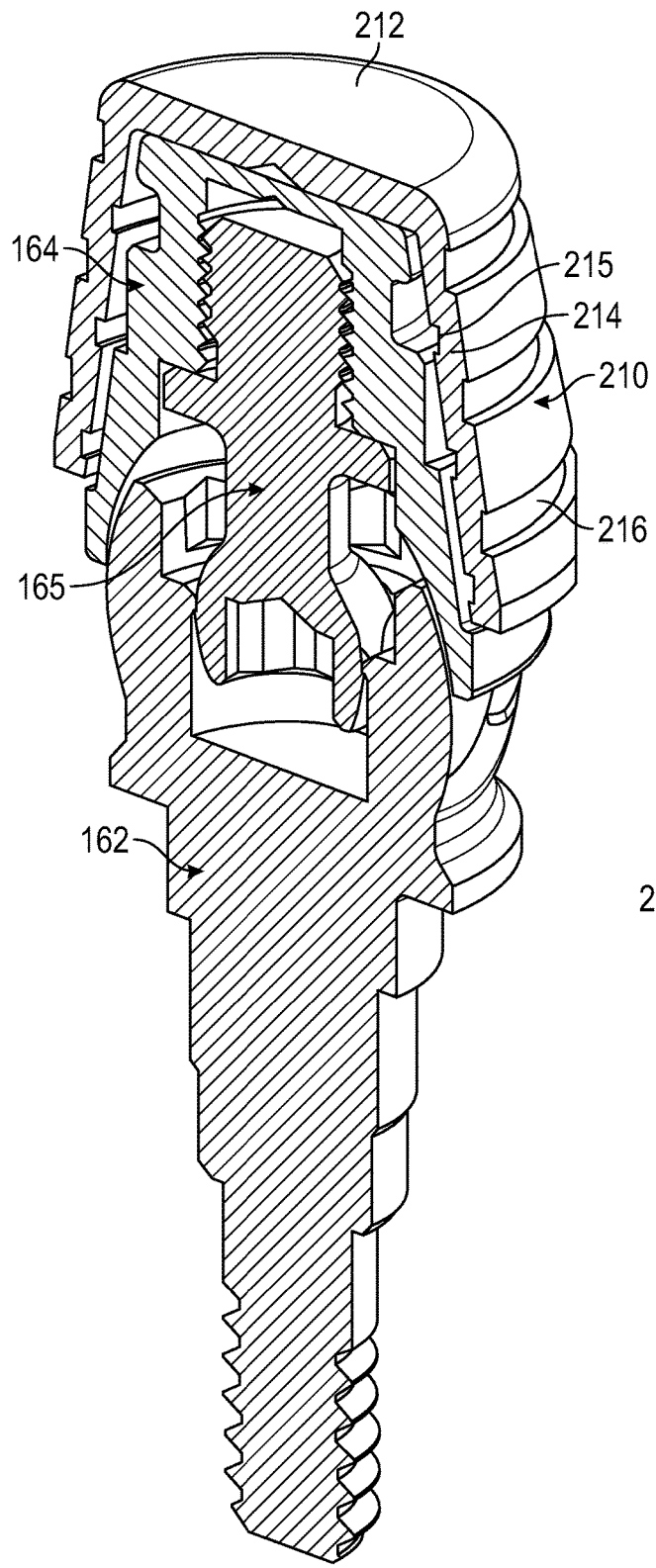
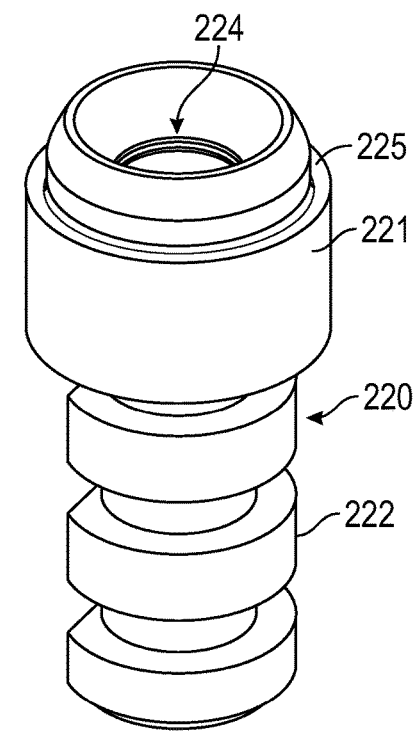
FIG. 39
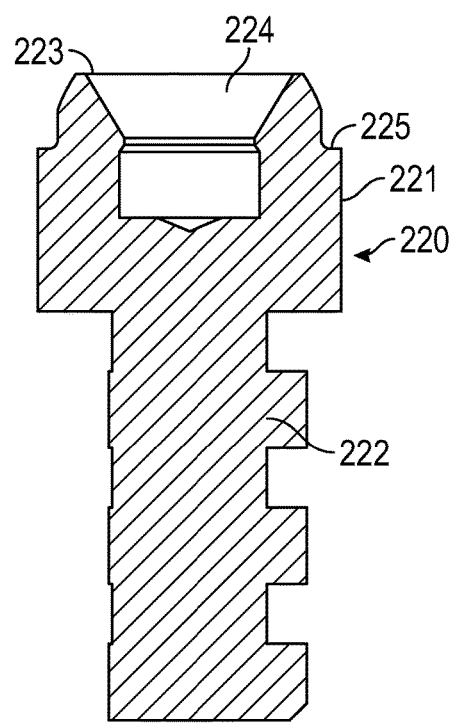
FIG. 38    FIG. 40

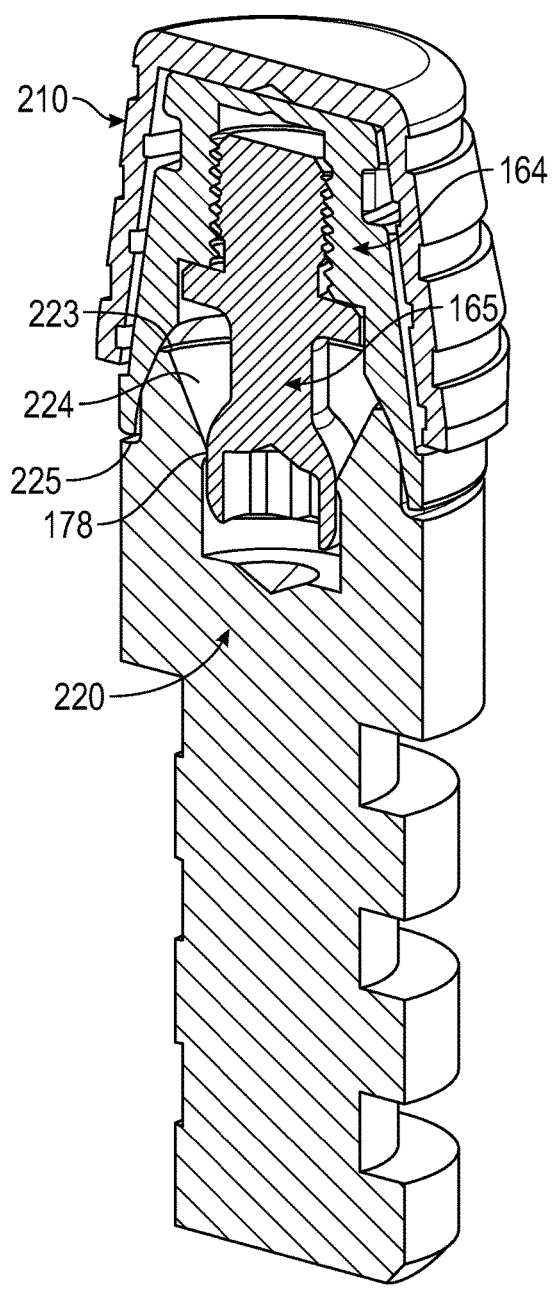
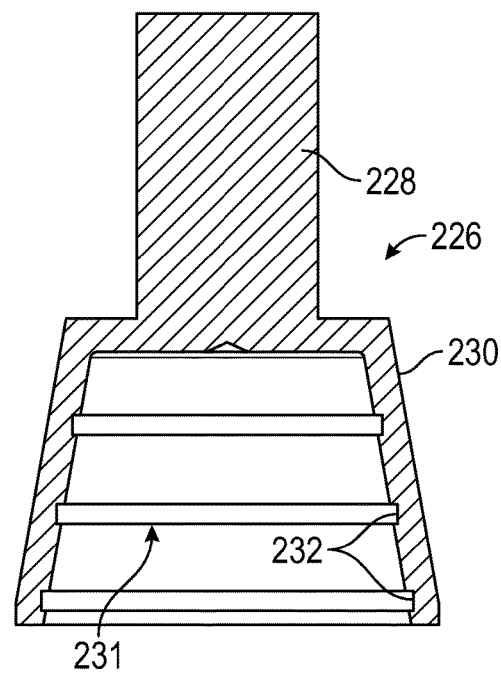
FIG. 41
FIG. 42

FIXED HYBRID DENTAL ATTACHMENT ASSEMBLY AND METHODS OF USE

CROSS-REFERENCE TO RELATED APPLICATIONS

This application is a continuation-in-part of co-pending U.S. patent application Ser. No. 14/806,616 filed on Jul. 22, 2015, which claims the benefit of Provisional Application Ser. Nos. 62/028,314 filed on Jul. 23, 2014 and 62/027,780 filed on Jul. 22, 2014, and the contents of each of the aforementioned applications are incorporated herein by reference in their entirety.

BACKGROUND

Field of the Invention

Devices and methods provided herein relate to a dental attachment assembly for anchoring a dental appliance with a base structure such as a tooth root or dental implant.

Related Art

Dental anchoring or attachment assemblies are utilized to anchor a dental appliance with a dental implant or tooth root, typically by fitting two or more partially-movable components together to provide an improved fit and comfort. In some assemblies, male and female parts have mating, snap engageable formations for releasably securing the male part to the female part. For example, the female part has a socket and the male part has a head for snap engagement in the socket. However, as repeated impacts of the socket and head may damage the retentive head of the male and cause wearing due to friction of the components as they move, a compressible annular ring may be provided to absorb the frictional forces and act as a cushion between the socket and the head. However, even the ring may wear out over a period of time and need to be replaced, requiring regular maintenance of the dental anchoring assembly that is uncomfortable and inconvenient for the patient. Furthermore, to allow the compressible annular ring to be easily removed and replaced, the ring may be provided with a securing mechanism on a mating surface with the socket (such as a threaded portion), which further adds to the cost and complexity of the dental anchor assembly.

It is therefore desirable to avoid the need for continued maintenance and simplify the design of the dental anchoring assembly.

SUMMARY

Embodiments described herein provide for a frictionally-retained detachable dental attachment assembly for adjustably attaching a dental appliance with a tooth root or implant. The dental attachment assembly includes a cap or denture attachment housing for securing in the dental appliance, an abutment for attachment to a tooth root or implant, and a retention member with a first end in fixed attachment with the cap and a second end in snap engagement with the abutment via a frictionally-retained ball or head of the retention member secured within a cavity of the abutment. The retention member is formed using a compressible material to allow the ball to compress and the retention member to flex while inserting the ball into the cavity. Additional friction-retained and fixed attachment configurations of the dental anchor device or attachment assembly are provided, along with methods of securing a dental appliance in a subject's mouth by means of the friction-retained and fixed attachment components of the attachment assembly.

In one aspect of the invention, a dental attachment assembly comprises a denture attachment housing for securing to a dental appliance, the housing having an open end defining an inner cavity; an abutment having an upper opening with a socket; and a retention member configured with a threaded portion to securely attach with the housing at a first end and configured with a compressible head or ball at a second end to frictionally engage with the socket of the abutment at a second end to form a frictional fit between the head and the socket and securely retain the dental appliance and abutment. In one embodiment, the socket has an annular inward projection or barb having an undercut, the projection having an inner diameter smaller than the outer diameter of the compressible spherical head, whereby the projection compresses and bites into an opposing portion of the spherical head to retain the head in the cavity, and the undercut resists removal of the head from the cavity.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which:

FIG. 8 is an exploded side elevation view illustrating a third embodiment of a dental attachment assembly which has an outer surface retention configuration;

FIG. 9 is an exploded cross-sectional view of the assembly of FIG. 8;

FIG. 22 is a side elevation view illustrating an embodiment of a screw-retained dental attachment assembly;

FIG. 23 is a cross-sectional view on the lines 23-23 of FIG. 22;

FIG. 38 is a cut-away view similar to FIG. 32 illustrating the denture attachment assembly of FIGS. 31 to 34 with the processing cap of FIGS. 36 and 37 engaged over the denture attachment housing;

FIG. 39 is a perspective view illustrating one embodiment of an abutment analog for use during model fabrication;

FIG. 40 is a vertical cross-section view of the abutment analog of FIG. 39;

FIG. 41 is a cut-away view similar to FIG. 38 illustrating the abutment analog of FIGS. 39 and 40 replacing the abutment in the denture attachment assembly of FIGS. 31 to 34 and with the processing cap of FIGS. 36 and 37 mounted on the denture attachment housing;

FIG. 42 is a vertical cross-sectional view of one embodiment of a waxing cap for creating a cavity in a cast framework in a wax-up procedure;

DETAILED DESCRIPTION

Figure 1:
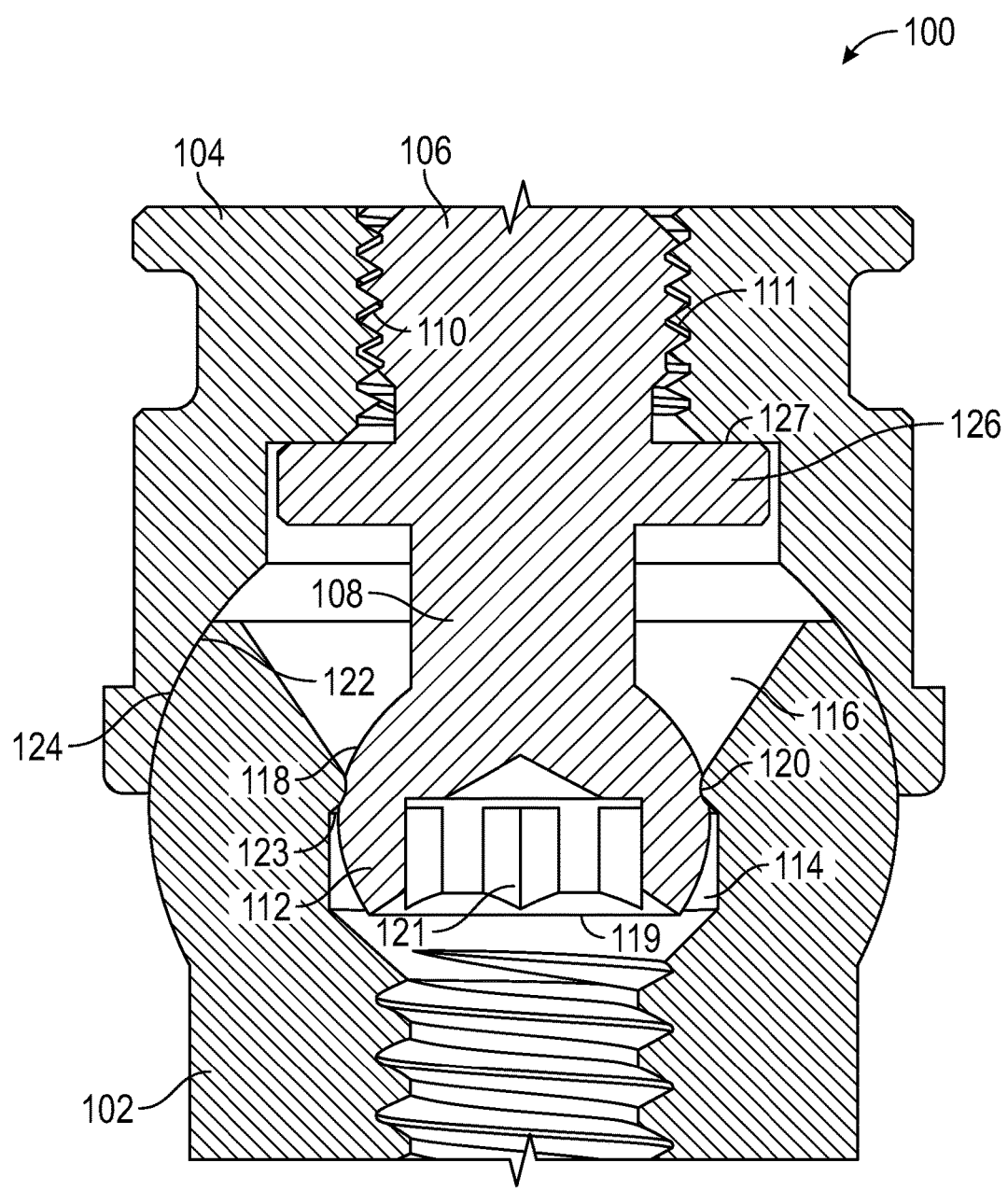
FIG. 1 is a vertical cross-sectional view of a first embodiment of a dental attachment assembly having a denture attachment housing, an abutment, and a retention member, with the parts shown in a fully assembled condition in which the denture attachment housing is secured to the abutment via the retention member.

Certain embodiments disclosed herein provide for a frictionally-retained detachable dental anchor device or dental attachment assembly for attaching a dental appliance with a tooth root or implant. The dental attachment assembly includes a cap or denture attachment housing secured in the dental appliance, an abutment attached with a tooth root or implant, and a compressible retention member with a first end in fixed attachment with the cap and a second end in snap engagement with the abutment via a frictionally-retained ball secured within a cavity of the abutment. The retention member is formed using a compressible material to allow the ball to compress and the retention member to flex while inserting the ball into the cavity. Additional friction-retained and fixed attachment configurations of the dental anchor device are provided, along with methods of securing a dental appliance in a subject's mouth by means of the friction-retained and fixed attachment dental anchor devices.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

The dental attachment assembly described herein functions similar to a fixed dental attachment system, yet can be more easily removed by a dental professional using a special tool. The dental attachment assembly described herein is useful to attach a dental appliance, such as a denture, with an implant and provide a retentive force of about 10 to 75 pounds, while also providing ease of engagement of the retention member with the abutment due to the compressible nature of the materials used and the friction-retained snap-fit of the ball and socket components.

As will be described in detail below, the retention member is formed from a compressible material—such as a polymer or soft metal—to allow the retention member to compress and flex while being attached or detached from an abutment secured to the implant. The compressible and flexible retention member can then be secured with the abutment at a variety of angles, which is often necessary when securing a dental appliance to a plurality of implants extending at different angles across a person's upper or lower mandible. Additionally, the compressible ball eliminates the need for a separate compressible annular ring to be positioned in the socket of the abutment between the retention member and interior abutment walls, as well as the need for a securing mechanism for securing the annular ring to the abutment walls. The dental attachment assembly is therefore easier to manufacture and requires less maintenance once inserted.

A. Dental Attachment Assembly

FIG. 1 illustrates one embodiment of a dental anchoring or attachment assembly 100 which may be attached with an implant (not shown) that may be anchored to a bone or other base structure (not shown) such as a tooth root. The assembly includes an abutment 102 which is secured to the implant and a cap or denture attachment housing (DAH) 104 which is secured in a recess of a dental appliance. A retention member 106 serves to provide the frictionally-retained connection between the cap and the abutment. To this end, the retention member includes a shaft 108 which has a threaded end portion 110 in a threaded connection with a corresponding threaded bore 111 in the cap. A second end of the shaft which interfaces with the abutment includes a head 112 which is substantially spherical in shape and which is configured to create a frictional fit with an inward projection or barb 120 in a socket 114 found in an upper opening 116 of the abutment. The head includes a curved surface 118 configured to frictionally engage an annular inward projection 120 in the socket, and a flat lower end face 119 with an inwardly directed hexagonal or polygonal shaped recess 121 for engagement with a suitable tool when the retention member is threadably engaged in bore 111 of cap 104. The inward projection has an undercut 123 that is engaged with the head 112. The socket does not necessarily need to be curved to match the curved surface 118 of the head 112. Instead, the head 112 is in contact with the socket only at projection 120 in most or all attachment orientations. In the embodiment in FIG. 1, the outer surface of the head 112 is convex, while the outer end face 119 of the head is flat in order to provide for a closer fit of the head 112 with the abutment. The inward projection 120 is configured to have a friction fit with the corresponding diameter of the head 112 at the mouth of the socket 114.

Figure 2:
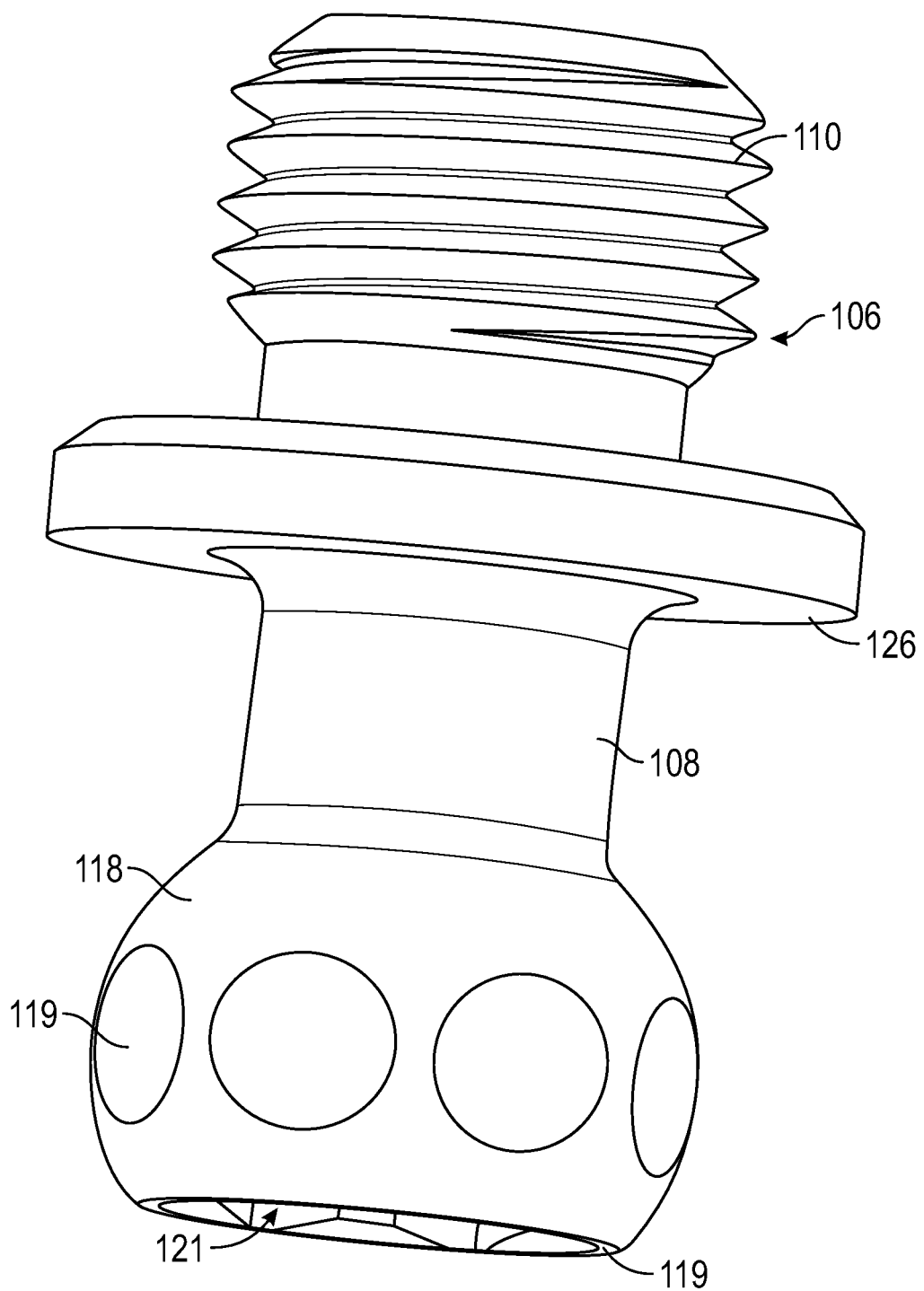
FIG. 2 is a perspective view of one embodiment of the retention member of FIG. 1.
Figure 3:
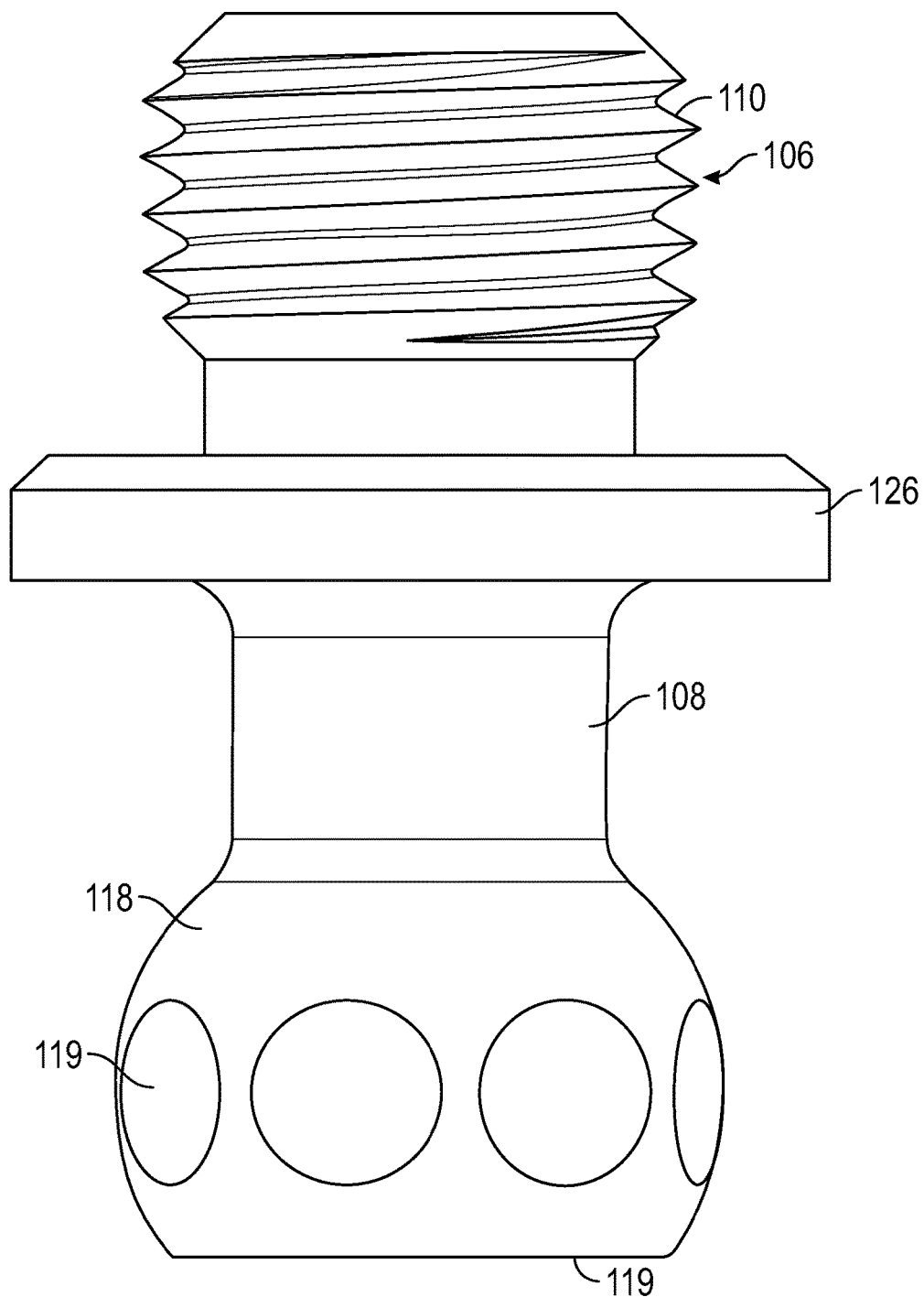
FIG. 3 is a side elevation view of the retention member of FIG. 2.

One benefit of the compressible material for the retention member 106 is that the diameter of the head 112 may be altered to increase or decrease the retentive force provided by the frictional-fit or compression of the head 112 engaging with undercut barb 123 of annular projection 120. The greater the maximum diameter of head 112, the higher the retentive force, since the inward projection cuts further into the head when fully engaged. A smaller diameter head 112 provides less retentive force. Retention force may also be varied by using different, softer or harder compressible materials for head 112, as described in more detail below in connection with the modified embodiment of FIGS. 31 to 35C. FIGS. 2 and 3 illustrate the external surface of the head 112 of one embodiment of retention member 106. The outer ball-shaped or convex curved surface 118 may have a series of flats or flattened portions 119 around the circumference of surface 118 to reduce the amount of friction between the curved surface 118 of the head and the corresponding curved surface or projection 120 of the socket. In an alternative embodiment, no flats are provided and the head has a smooth outer convex surface. A smooth convex surface increases the amount of friction between head 112 and projection 120, since the projection digs more deeply into the compressible surface of the head in the attached configuration of FIG. 1. Thus, one, two, or all of the following parameters may be used to vary the retention force of the head in the abutment socket: head diameter, head shape, and the selected compressible material of the head. The retention force may vary from anywhere between about 10 to about 75 pounds, although some embodiments may provide as little as about 1 pound of retention force for use in the initial positioning of the dental appliance and dental anchoring device.

The cap 104 is configured with an annular internal surface 122 which may be curved to engage with a corresponding curved outer surface 124 of the abutment, providing an additional frictional fit for the dental attachment assembly.

In one embodiment, a ball flange 126 is provided on shaft 108 at a predetermined spacing below threaded portion 110. Flange 126 extends perpendicular to the axial direction of the shaft 108 and acts as a stop by engaging an opposing surface 127 of the cavity in cap 104 when threaded stem 110 is threaded into bore 111. The ball flange 126 serves to help locate the ball 112 within the socket 114 and cap 104 and prevent vertical movement of the assembly.

In the embodiment described herein, the retention member may be formed from a compressible or elastomeric material such as a polymer or a soft metal, non-limiting examples of which include polymers such as polyether ether ketone (PEEK), polyoxymethylene or acetal polymers such as Delrin®, and soft metals such as nickel titanium (nitinol), pink TiCN (titanium carbo nitride) or titanium. The soft metal may be a coating on the surface of the head portion in some embodiments. In one embodiment, the surfaces may be coated with a gold nitride coating to reduce friction.

Figure 4:
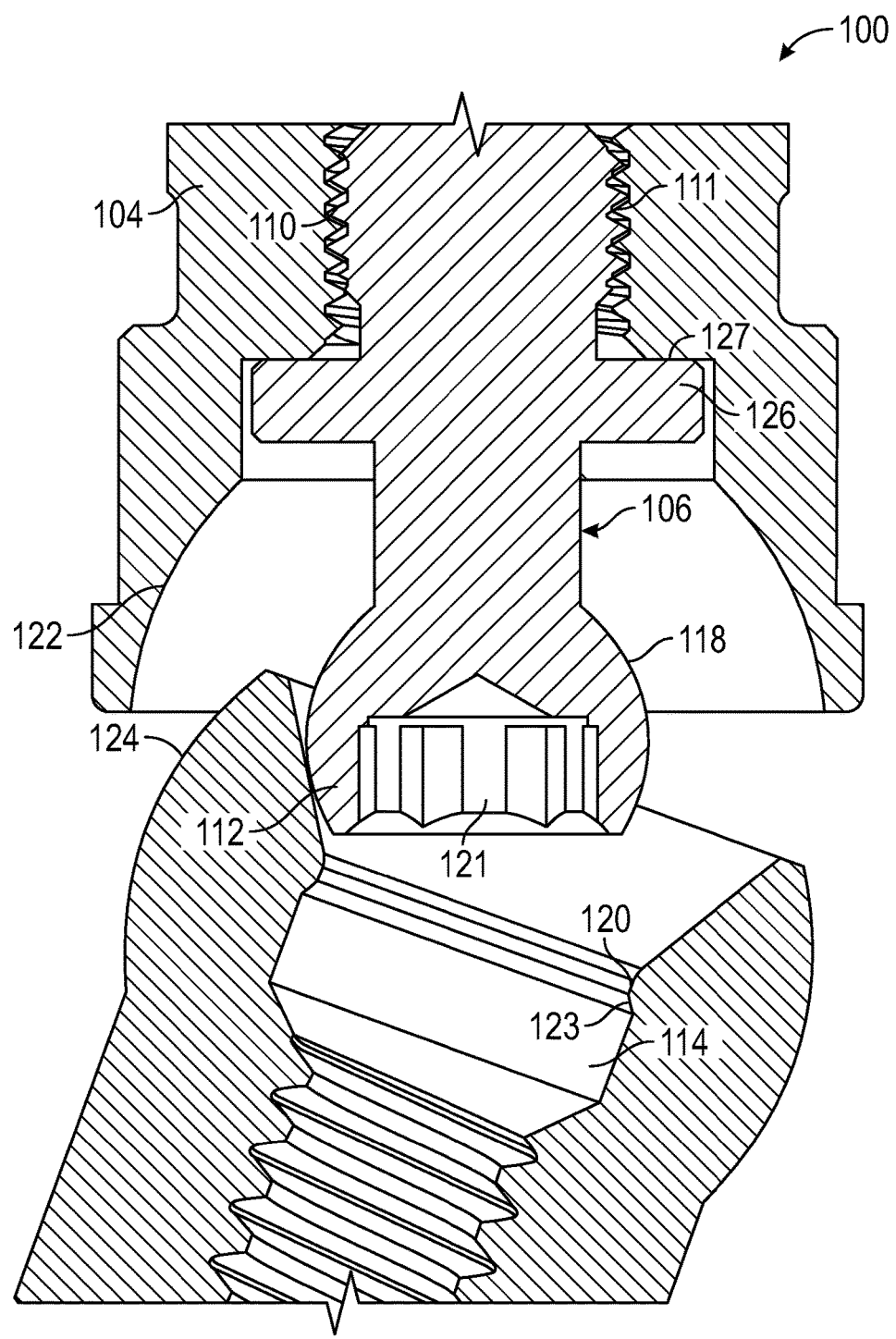
FIG. 4 is a vertical cross-sectional view of the dental attachment assembly of FIG. 1 in an angled, unattached configuration during assembly of the parts.

FIG. 4 illustrates the dental attachment assembly in an angled, unattached configuration prior to full insertion of head 118 in socket 116, 114, illustrating the varying angles at which the retention member 106 may be snap-fit into the abutment. In practical applications, the implant may protrude from the bone or tooth root at varying angles from the ideal vertical angle due to the structure of the bone or the placement of the implant during surgery. The dental anchoring or attachment assembly therefore corrects any angular displacement by rotation of the head 112 in the socket 114. In one embodiment, the angle of approach of the head with respect to the abutment may vary up to about 20 degrees in any direction from the vertically-aligned orientation shown in FIG. 1. In combination with another implant also offset at a similar angle, the dental anchoring device may therefore provide as much as about 40 degrees of angle correction.

Figure 5:
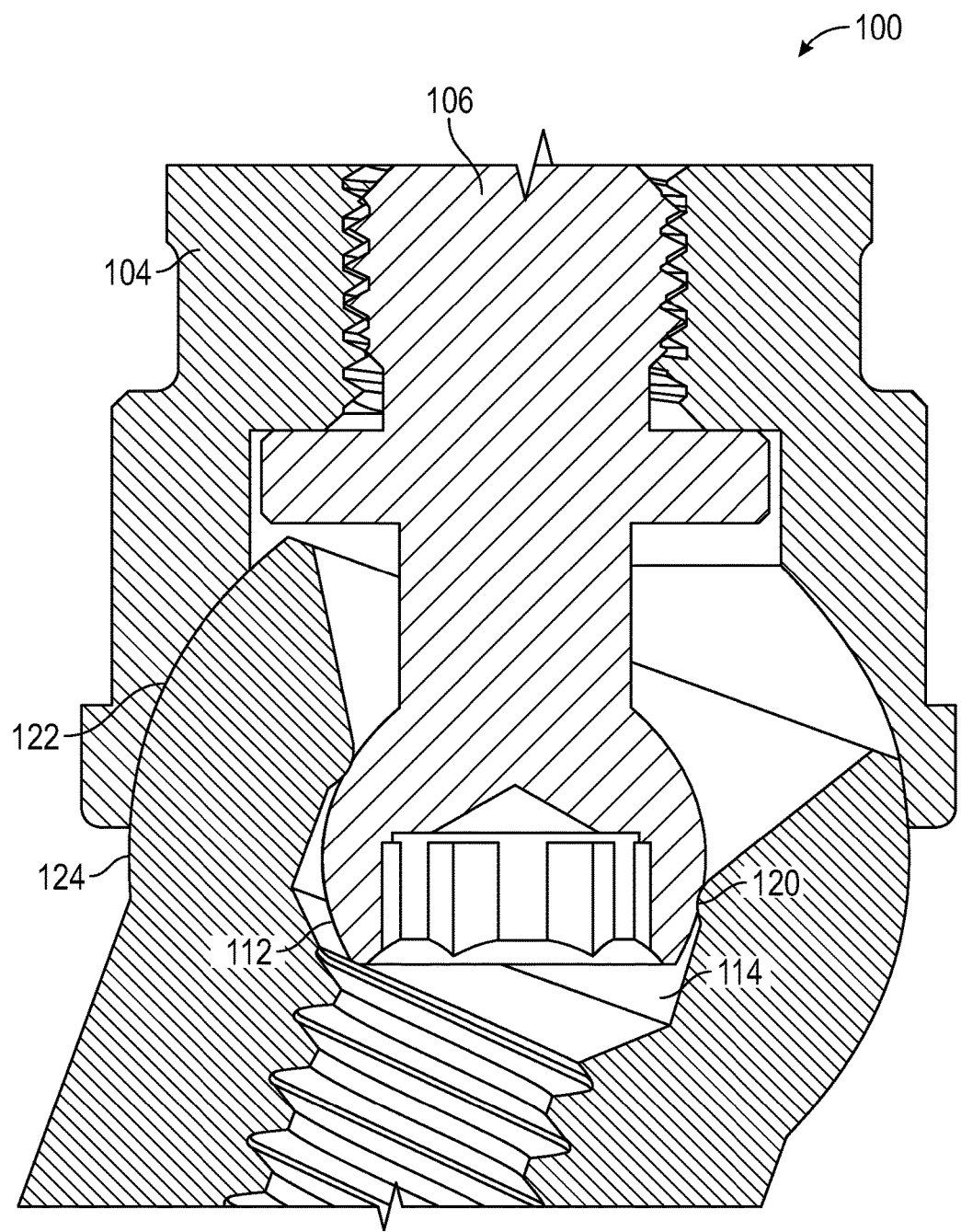
FIG. 5 is a vertical cross-sectional view of the dental attachment assembly of FIGS. 1 and 4 in an attached, angled configuration as compared to the aligned configuration of FIG. 1.

FIG. 5 illustrates of the dental attachment assembly in the angled orientation shown in FIG. 4 but where the retention member 106 is now snap-fit into the socket 114 of the abutment 102. As illustrated in FIG. 5, the head 112 may be secured within the socket 114 despite the differential angle. Furthermore, the annular surface 122 of the cap 104 is also still frictionally engaged around the outer curved surface 124 of the abutment with the offset indicated in FIG. 5, and the annular projection 120 is frictionally engaged at an angle around the opposing annular surface portion of head 118.

Figure 6A:
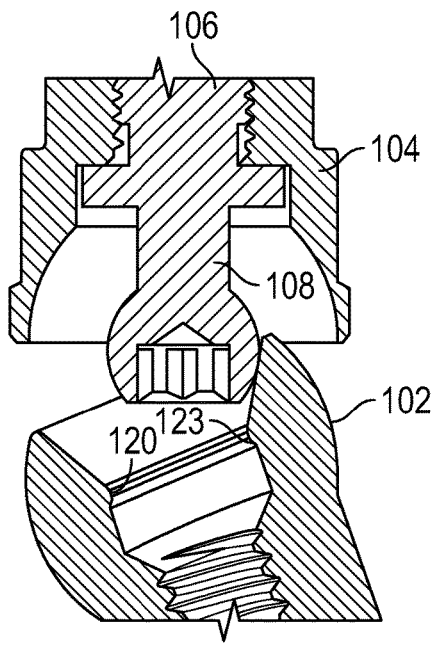
FIGS. 6A, 6B and 6C are cross-section views illustrating steps of a process of attaching the retention member with the abutment in the assembly of FIGS. 1 to 5, illustrating a compression of a ball and shaft portion of the retention member, according to an embodiment of the invention.
Figure 6C:
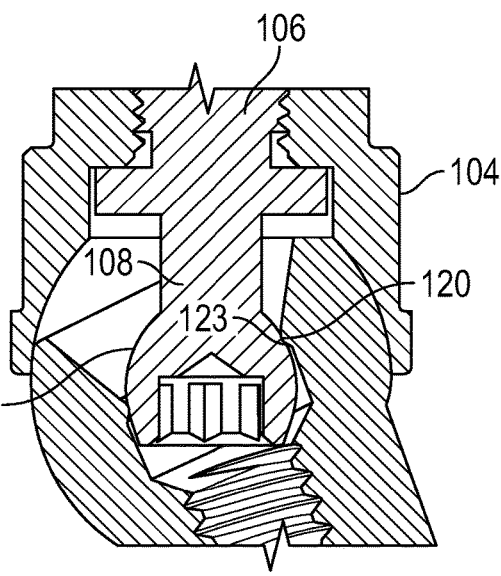
Figure 6B:
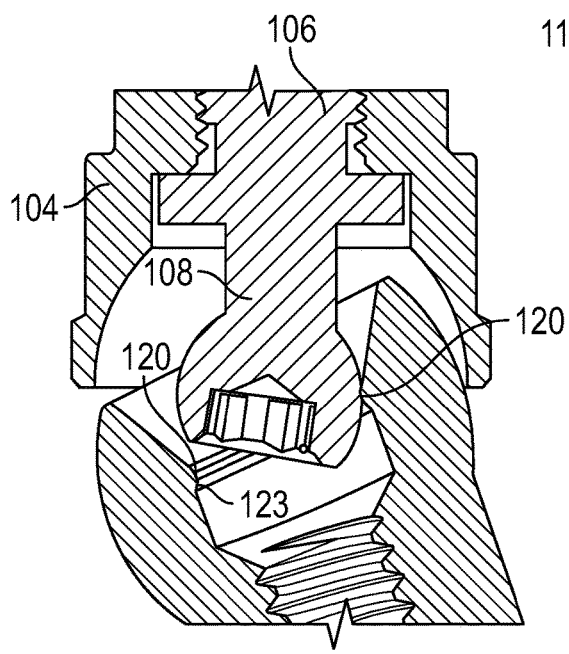

FIGS. 6A-6C are side cutout view illustrations of the flexing and compression of the head 112 and shaft 108 of the retention member 106 during a process of attaching the retention member with the abutment at the angle already illustrated in FIGS. 4 and 5, according to an embodiment of the invention. As noted above, the retention member 106 is made of a compressible polymer or soft metal material which is also capable of flexing in the case of engagement with an offset abutment. As illustrated specifically in FIG. 6B, the shaft 108 and head 112 of the retention member 106 are flexing and compressed due to the angle of the abutment with respect to the retention member 106. However, as shown in FIG. 6C, once the retention member 106 is frictionally snap-fit into the socket 114, the flexure and compression is reduced such that the retention member 106 and abutment 102 provide a secure fit without inducing an undue amount of stress on the retention member. At the same time, annular projection or barb 120 compresses or bites into opposing regions of the curved surface 118 of head 112, securing cap 104 to abutment 102.

B. Screw-Retained Configuration

Figure 7:
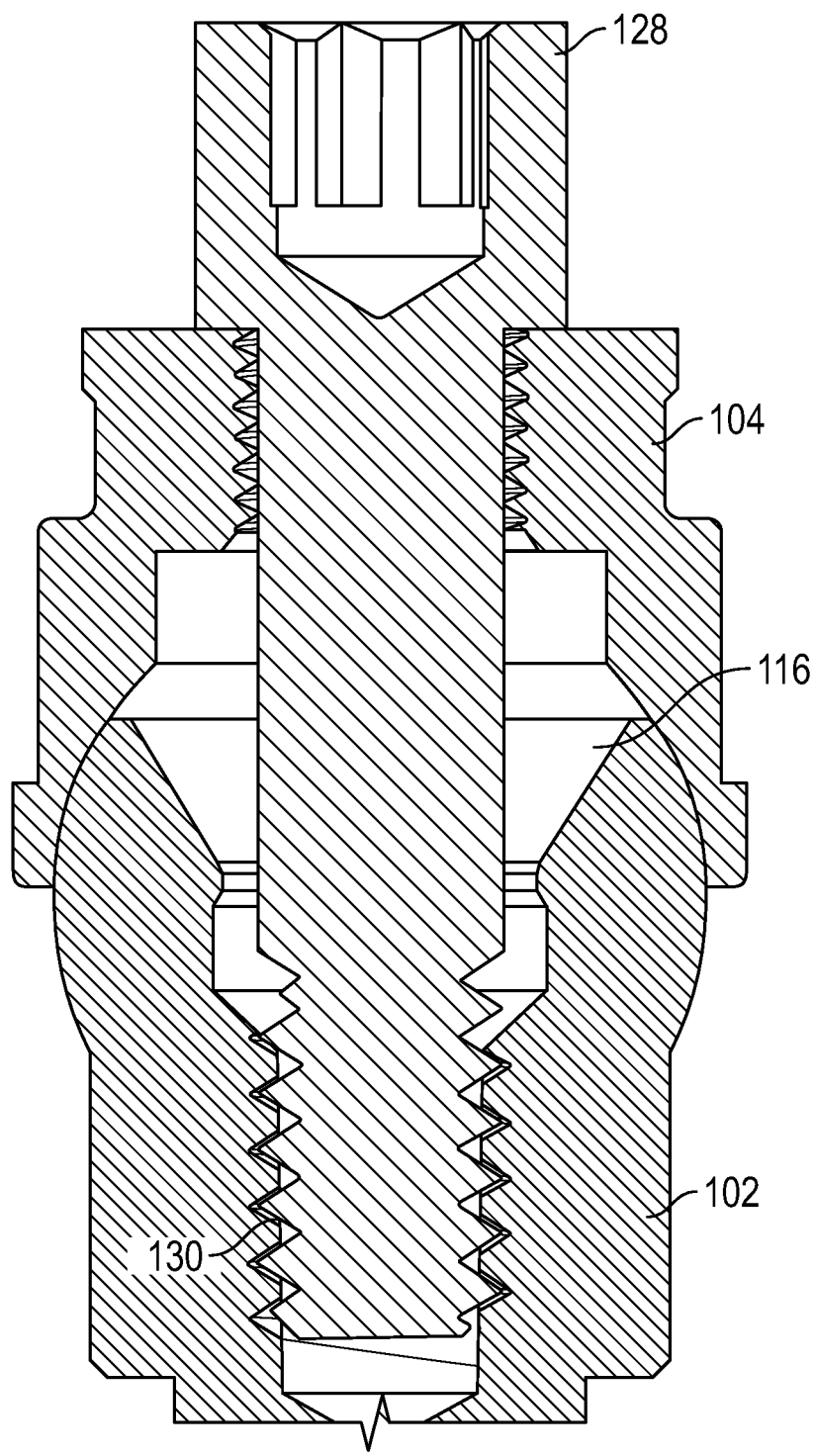
FIG. 7 is a vertical cross-sectional view illustrating a second embodiment of a dental attachment assembly.

FIG. 7 illustrates a modified, screw-retained dental attachment assembly, according to another embodiment of the invention, where instead of the ball and socket configuration, a cantilevered screw 128 protrudes through the cavity 116 in the abutment 102 and forms a threaded connection 130 with a corresponding threaded bore in the abutment 102 to create a fixed connection. As illustrated above with regard to FIG. 1, the annular surface 122 of the cap 104 provides a sliding retentive surface with the outer curved surface 124 of the abutment to allow for minimal rotation of the screw 128 and cap 104 with respect to the abutment.

This embodiment is useful for obtaining a highly secure fit between an implant and the dental appliance which will provide a significant retentive force. As described further below, this configuration may only be needed for one implant where several implants are being used to secure a dental appliance across the surface of a person's mouth.

C. Outer Surface Retention Configuration

In another alternative embodiment illustrated in FIGS. 8 and 9, an abutment 132 is utilized with a cap-like retention member 134 and a denture cap 136 to provide retentive force on the outer surface of the abutment without the use of the head and socket configuration. FIGS. 8 and 9 are exploded side elevation and cross-sectional illustrations, respectively, of the denture cap 136, retention member 134 and abutment 132 of an outer surface retention configuration of a dental attachment assembly, according to an embodiment of the invention. As illustrated herein and also above in FIG. 1, the outer surface 124 of the abutment 130 forms a curved surface which mates with a corresponding curved surface 122 of the retention cap 132 to form a frictional fit. The retention member 134 has a threaded portion 138 configured for threaded engagement in corresponding threaded bore 140 in denture cap 136. In this embodiment, bore 140 is not a through bore through the cap but instead terminates in the cap, and has a closed top or end wall 141. The threaded bores in the denture caps of any of the preceding embodiments may also have similar closed end walls in alternative embodiments.

Figure 10:
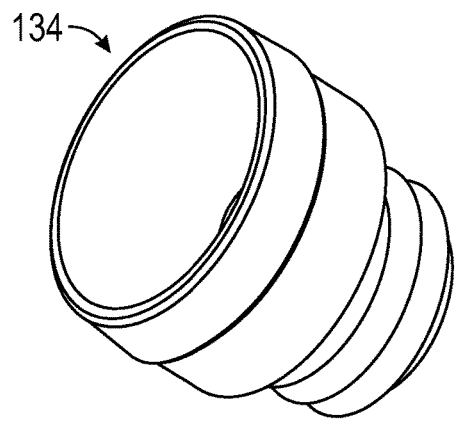
FIG. 10 is a bottom side perspective view illustration of the retention member of the assembly of FIGS. 8 and 9.
Figure 11:
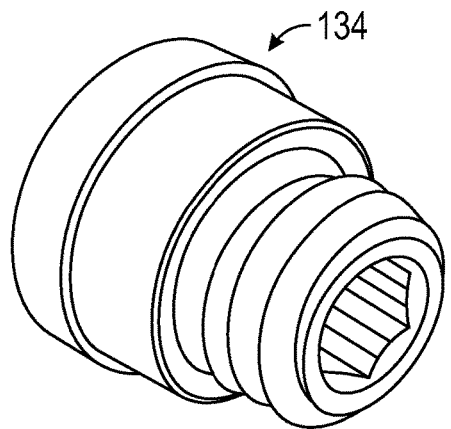
FIG. 11 is a top side perspective view illustration of the retention member of FIG. 10.
Figure 12:
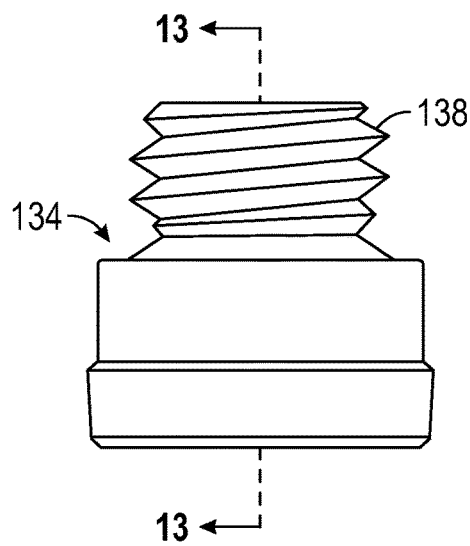
FIG. 12 is a side view illustration of the retention member of FIGS. 10 and 11.
Figure 13:
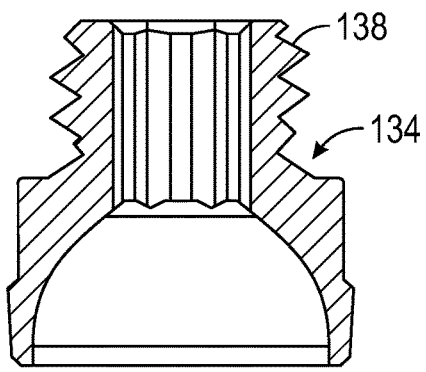
FIG. 13 is a cross-sectional view of the retention member on the lines 13-13 of FIG. 12.
Figure 14:
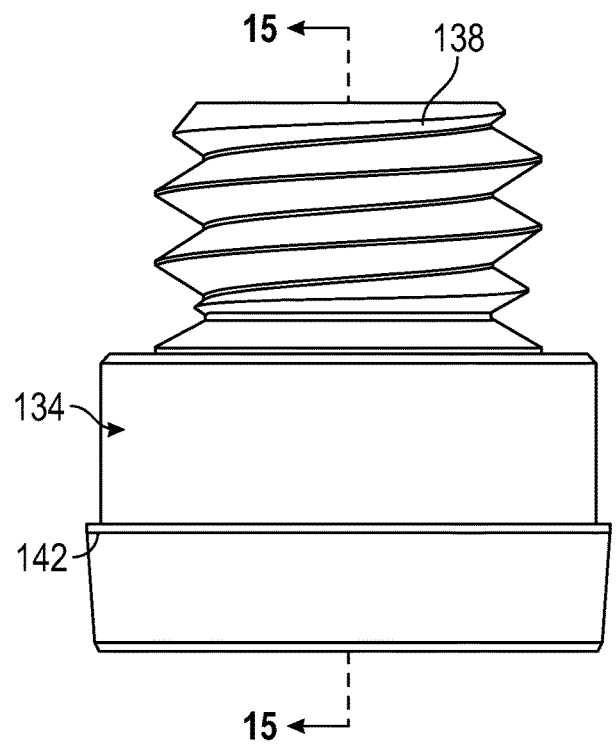
FIG. 14 is a side view illustration of an embodiment the retention member with an acrylic finishing line.
Figure 15:
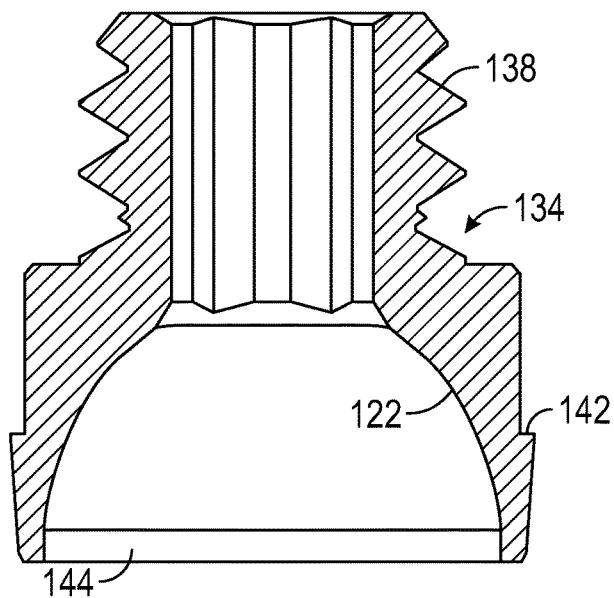
FIG. 15 is a cross-sectional view of the retention member along lines 15-15 of FIG. 14.

FIGS. 10 to 13 are illustrations of the retention cap or member 134 of the outer surface retention assembly of FIGS. 8 and 9, according to an embodiment of the invention, showing the threaded surface 138. FIGS. 10 and 11 are perspective views taken from opposite ends of retention cap 134, while FIGS. 12 and 13 are side elevation and cross sectional views, respectively. FIGS. 14 and 15 illustrate retention cap 124 with an acrylic finishing line 142 where acrylic from the surrounding denture can create a smooth finish with the denture cap, according to an embodiment. FIG. 15 illustrates inner spherical retention surface 122 of the retention member 134 which has an outer vertical surface 144 which serves as a wraparound retentive feature.

Figure 16:
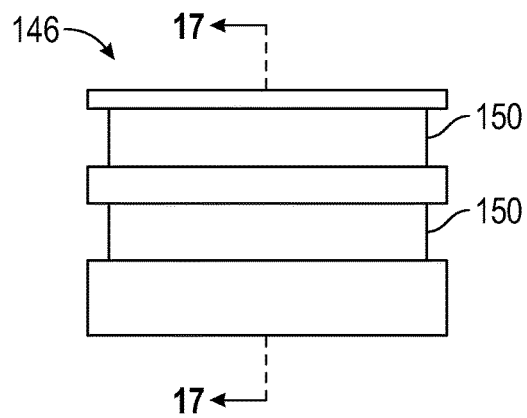
FIG. 16 is a side elevation view of an acrylic pick up cap embodiment of the denture cap.
Figure 17:
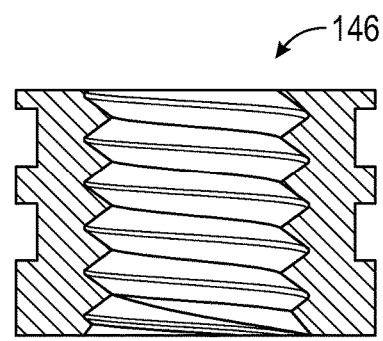
FIG. 17 is a cross-sectional view of the acrylic pick up cap along lines 17-17 of FIG. 16.
Figure 18:
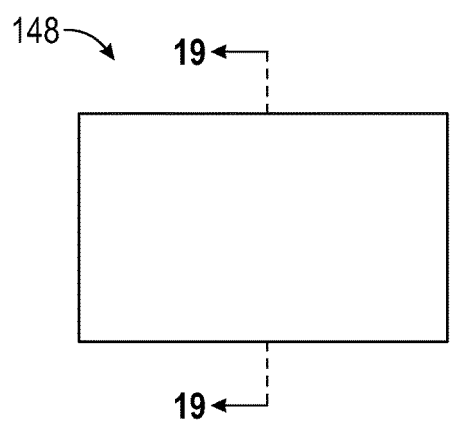
FIG. 18 is a side elevation view of a burn out cap embodiment of the denture cap, according to an embodiment of the invention.
Figure 19:
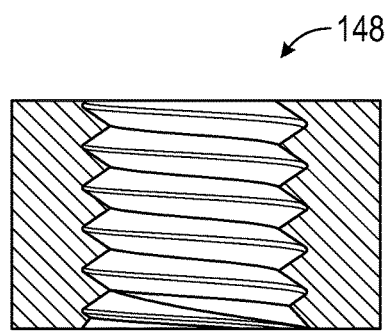
FIG. 19 is a cross-sectional view of the burn out cap along lines 19-19 of FIG. 18.

FIGS. 16 and 17 are side elevation and cross-sectional views, respectively, of an acrylic pick up cap 146 embodiment of the denture cap 136, according to an embodiment of the invention; and FIGS. 18 and 19 are side elevation and cross-sectional illustrations, respectively, of a burn out cap 148, according to an embodiment of the invention. The acrylic pick up cap 146 includes a plurality of retaining channels 150 that acrylic will flow through to hold a dental appliance such as a denture with the cap 146. The burn out cap 148 is used in cast bar situations.

Figures 20, 21:
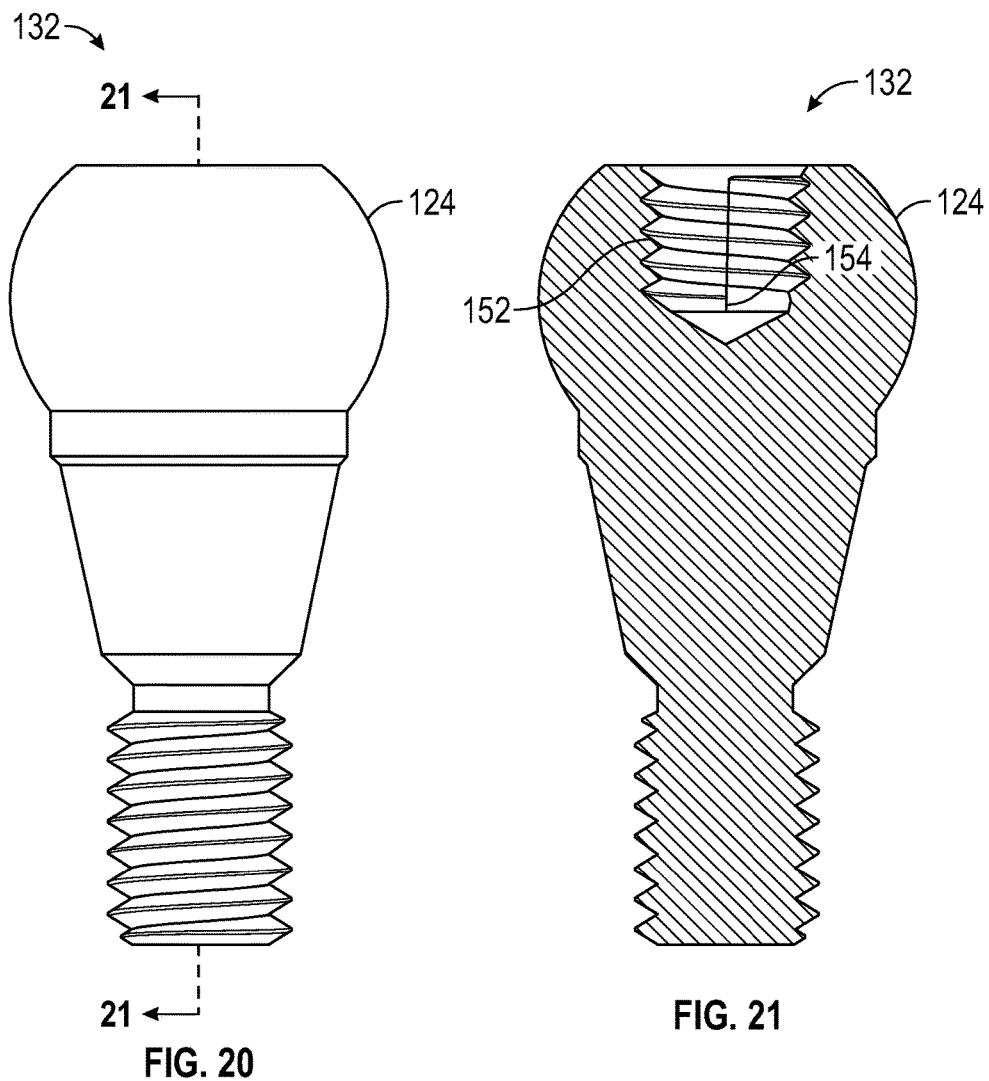
FIG. 20 is an enlarged side elevation view of the abutment of the assembly of FIG. 8.
FIG. 21 is a cross-sectional view of the abutment on the lines 21-21 of FIG. 20.

FIGS. 20 and 21 are side elevation and cross-sectional views, respectively, of the abutment 132 of the outer surface retention configuration of FIGS. 8 and 9, according to an embodiment of the invention. The abutment has an internal thread 152 for securing threaded components such as a healing collar, impression coping screw and Cantilever screw during processing. Additionally, an internal driving feature 154 is visible, which serves to tighten the abutment into the implant.

Figures 24, 25:
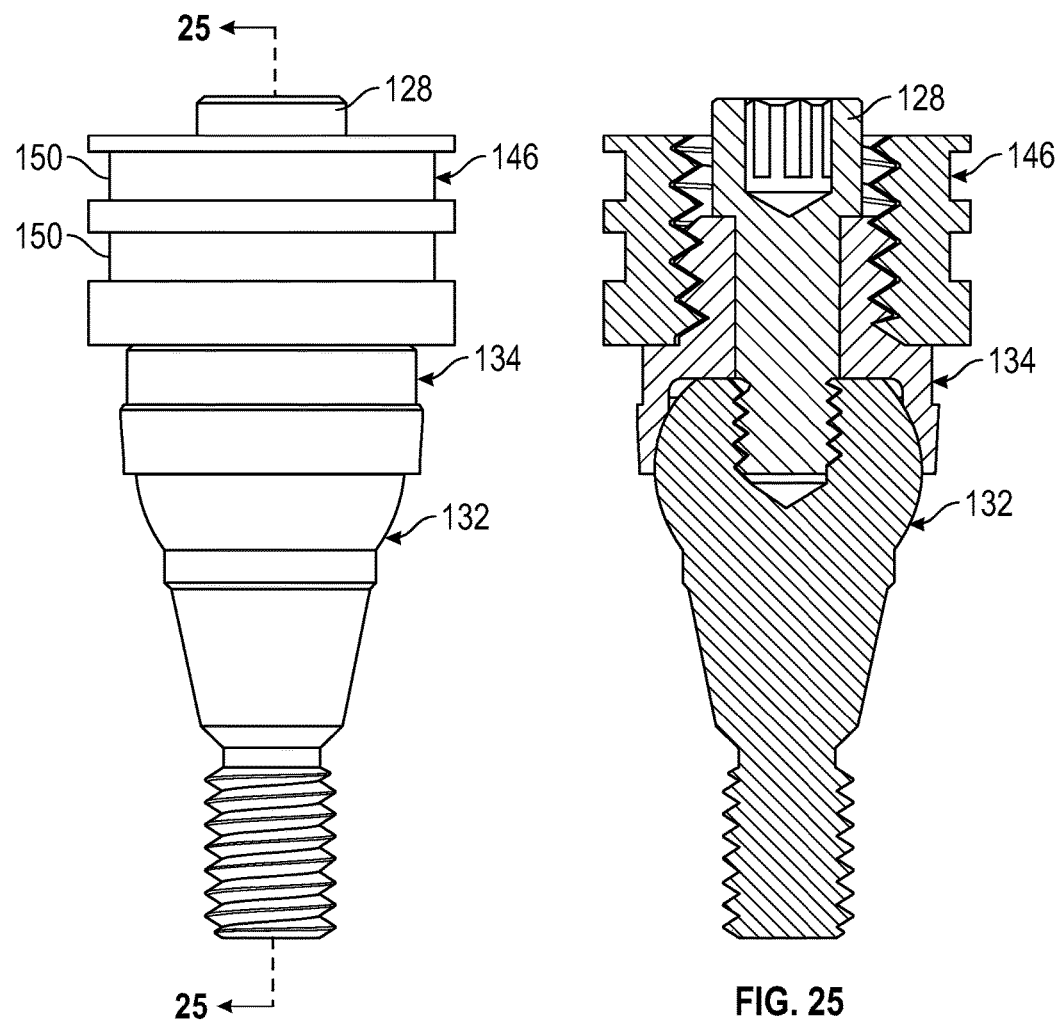
FIG. 24 is a side elevation view of the assembly of FIGS. 22 and 23 with an added acrylic pick up cap.
FIG. 25 is a cross-sectional view on the lines 25-25 of FIG. 24.

FIGS. 22 and 23 are side elevation and cross-sectional views, respectively, of a screw-retained embodiment of the outer surface retention configuration, according to an embodiment of the invention, where a cantilever screw 128 as illustrated in FIG. 7 is secured through an opening 129 of the retention cap 134 and into a threaded connection with the abutment 132. Screw 128 has a threaded end portion 137 which engages the internal thread 152 of abutment 132. FIGS. 24 and 25 are side elevation and cross-sectional views, respectively, of acrylic pick up cap 146 of FIGS. 16 and 17 in use with the retention cap 134 and abutment 132 of screw-retained embodiment of FIGS. 22 and 23, according to an embodiment. Pick up cap 146 is threaded onto the other threaded portion 138 of retention cap or member 134, and screw 128 is engaged through the open end of pick up cap 146 and through bore 129 of retention member 134 to engage the threaded bore 152 in abutment 132.

Figure 26:
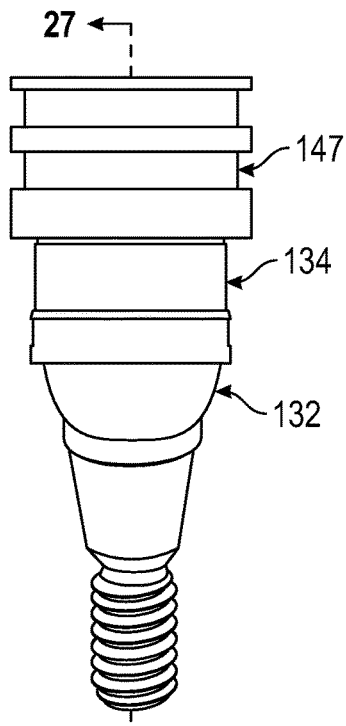
FIG. 26 is a side elevation view of the assembly of FIGS. 24 and 25 in an angled configuration.
Figure 27:
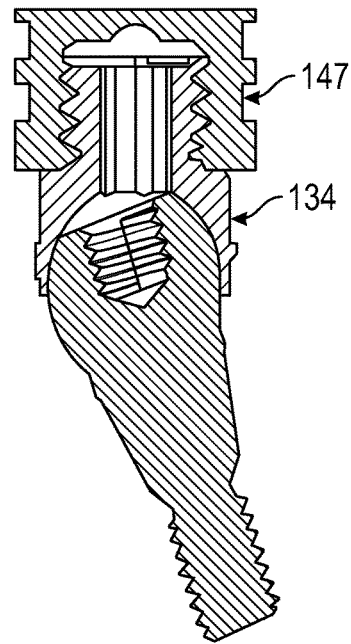
FIG. 27 is a cross-sectional view on the lines 27-27 of FIG. 26.
Figure 28:
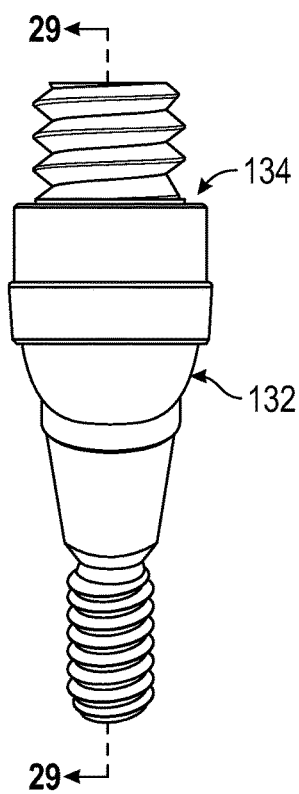
FIG. 28 is a side elevation view of the outer surface retention configuration of FIG. 8 in an angled orientation.
Figure 29:
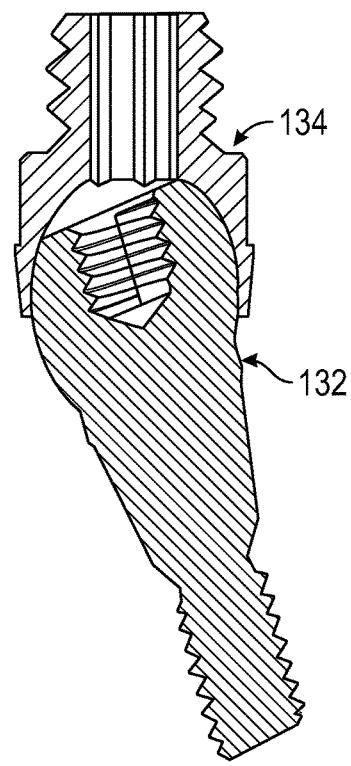
FIG. 29 is a cross-sectional view on the lines 29-29 of FIG. 28.

As illustrated, FIGS. 26 and 27 are side elevation and cross-sectional views, respectively, of the outer surface retention configuration in an angled orientation, according to an embodiment, with a modified acrylic pick up cap 147 similar to cap 146 of FIGS. 24 and 25 but having a closed upper end. FIGS. 28 and 29 are similar side elevation and cross-sectional views, respectively, of the outer surface retention configuration excluding the acrylic pick up cap 147.

D. Method of Use

Figure 30:
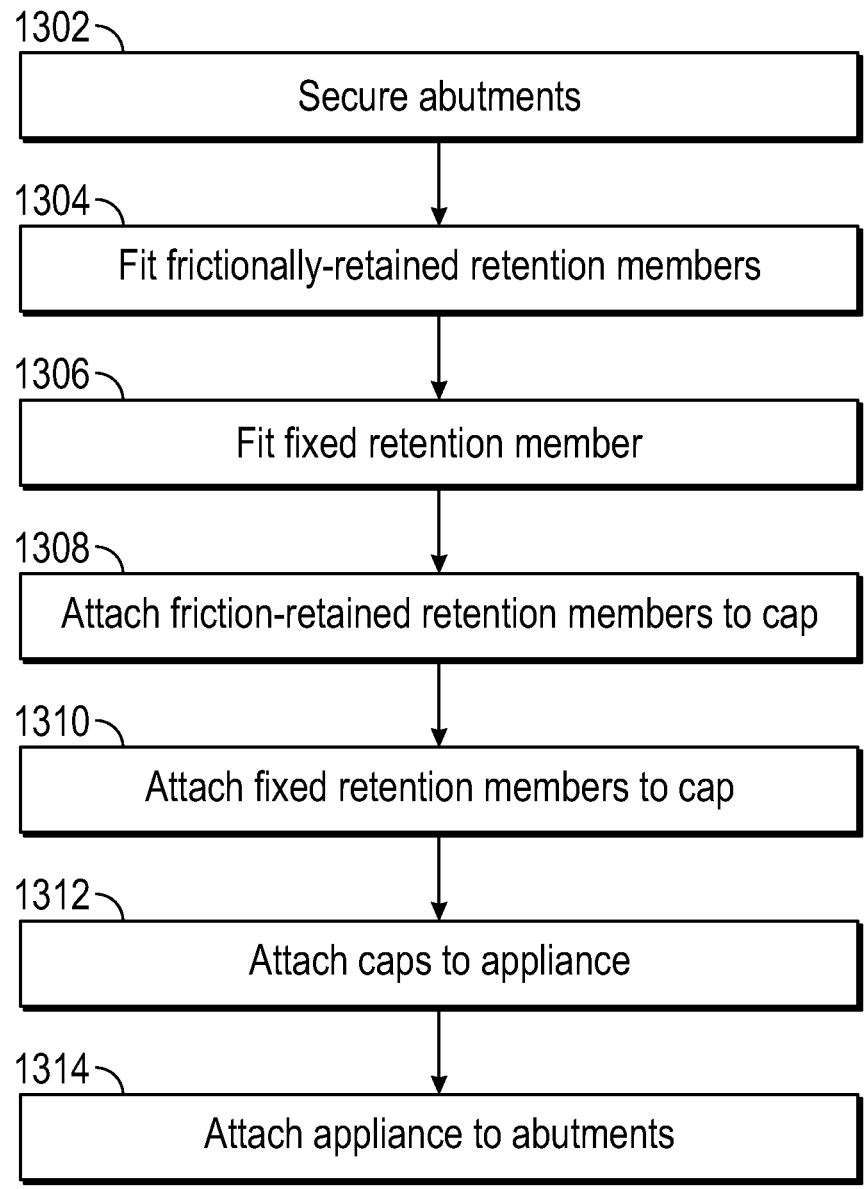
FIG. 30 is a flow diagram of one embodiment of a method of attaching a dental appliance with at least one dental attachment assembly.

FIG. 30 illustrates one embodiment of a method of attaching a dental appliance to a plurality of implants using the various dental attachment assemblies described above. For example, where a patient is being fitted with a complete upper or lower denture, a plurality of implants will be inserted into the bone structure across the area where the denture is to be placed. In some embodiments, as few as 2 or as many as 6 implants may be used. In the embodiments described herein, the frictionally-retained dental attachment assembly may be utilized for the majority of the implants while fewer of the implants—even just one—utilize the fixed, or screw-retained, dental attachment assembly. This provides flexibility in attaching the majority of the implants with the dental appliance while still providing a fixed connection at one implant which will ensure the retention of the entire dental appliance against any amount of retentive force.

In a first step 1302, an abutment is secured to an implant or other root structure that will support the dental appliance. Next, the frictionally-retained retention members are fitted onto at least one abutment (step 1304), and at least one fixed retention member is attached to at least one abutment (step 1306). In step 1308, the friction-retained retention members are attached to their respective caps, and in step 1310, the fixed retention members are attached to their respective caps. In step 1312 the non-swiveling retention member is removed from the cap and a swiveling retention member is inserted into the cap. In step 1312, the dental appliance may be engaged onto the abutment by the snap engagement of the retention member onto the abutment and may be swiveled or rotated into place through use of the swivel joint between the cap and retention member, which is further enhanced by the concave recess within the cap.

E. Modified Dental Attachment Assembly

Figure 31:
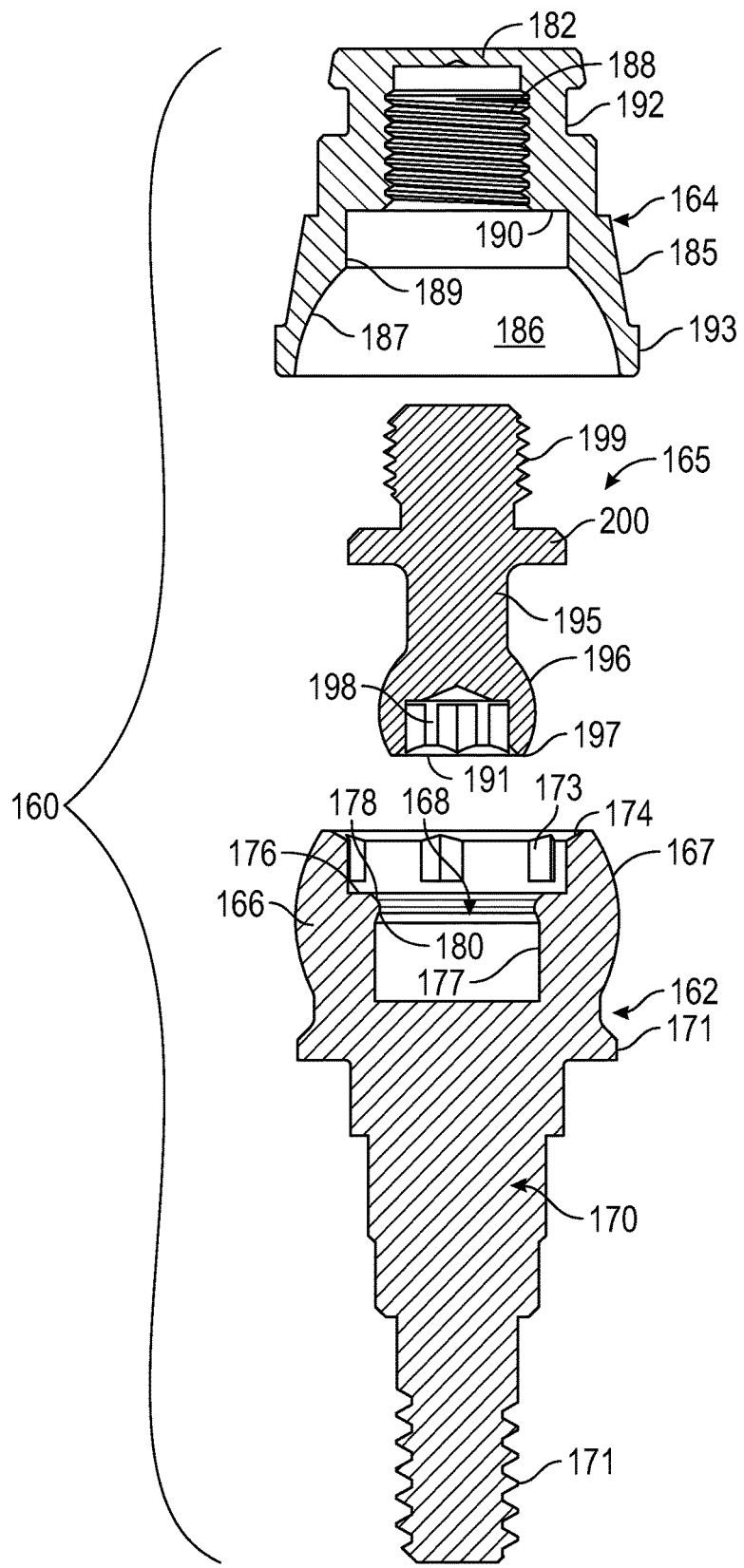
FIG. 31 is an exploded cross-sectional view of another embodiment of a dental attachment assembly.
Figures 32, 33:
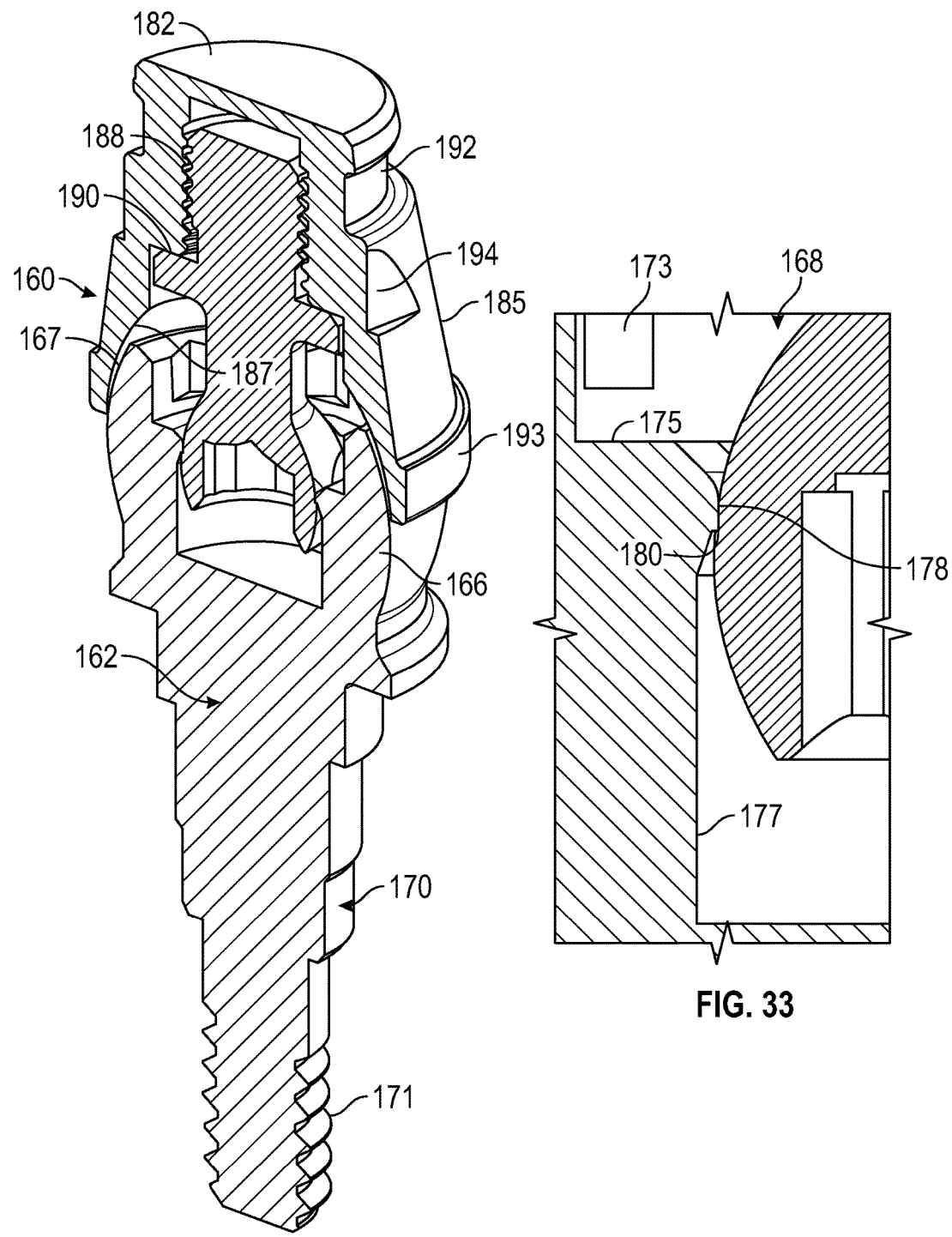
FIG. 32 is a cut-away view of the assembly of FIG. 31 in a fully assembled condition.
FIG. 33 is an enlargement of part of the assembly in FIG. 32 illustrating the engagement between a barb or projection in the socket and the ball or head of the retention member.

FIGS. 31 to 34 illustrate another embodiment of a dental attachment assembly 160 which has a similar retention member to the embodiment of FIGS. 1 to 6C but has a modified abutment 162 for attachment to a tooth root or dental implant, and a modified cap or denture attachment housing (DAH) 164 for securing in a dental appliance. Retention member 165 secures denture attachment housing 164 to abutment 162, as illustrated in FIG. 32. A plurality of retention members of different materials or ball shapes or dimensions may be provided for providing a range of different retention forces based on the installation force requirement, as described in more detail below in connection with FIGS. 35A to 35C.

Abutment 162 has a head portion 166 with a rounded or convex outer surface 167, a socket 168 extending inwardly into head portion 166, and a shaft 170 extending away from head portion 166 for engagement in a corresponding mating bore in a tooth root or implant. Shaft 170 has a series of cylindrical portions of stepped diameter extending from flange 171 at the lower end of head portion 166, and an externally threaded end portion 172. Abutment 102 of the first embodiment had an internal hex drive 114 below the projection or barb 120, at the inner end of the socket. Abutment 162 of this embodiment instead has a hex drive portion 173 close to a tapered entrance opening 174 at the outer end of socket 168, which is easier to access with a removal or insertion tool than the internal hex of the first embodiment. Additionally, the screw threaded bore extending from the socket into the shaft as seen in FIG. 1 to allow screw retention is removed. This eliminates a food trap which is difficult to clean, and also reduces fabrication complexity. Elimination of this threaded bore also increases strength of the abutment and increases the amount of clearance provided for the head or ball portion of the retention member. In one embodiment, the hex drive portion 121 of the first embodiment was a 0.050 inch hex drive. In one embodiment of abutment 162, hex drive portion 173 at the entrance opening is a 0.100 inch hex drive. Removing the internal threads and internal hex at the inner end of the abutment socket allows some abutments to be shorter in length due to thicker walls.

A step 176 is provided at the lower end of hex drive portion 173, and is followed by a reduced diameter portion 177 of the socket. An annular, inwardly directed projection or barb formation 178 is located at the top of socket portion 177. Annular projection 178 is similar in function to projection 120 of the first embodiment, but is of different shape, as seen in FIGS. 31 to 33. Projection 178 has a rounded convex portion with an undercut 180 which forms a sharp edge or barb which tends to dig into an opposing surface of the head portion of retention member 165 to resist removal of the retention member from the socket, as described in more detail below and illustrated in the enlarged view of FIG. 33.

Figure 34:
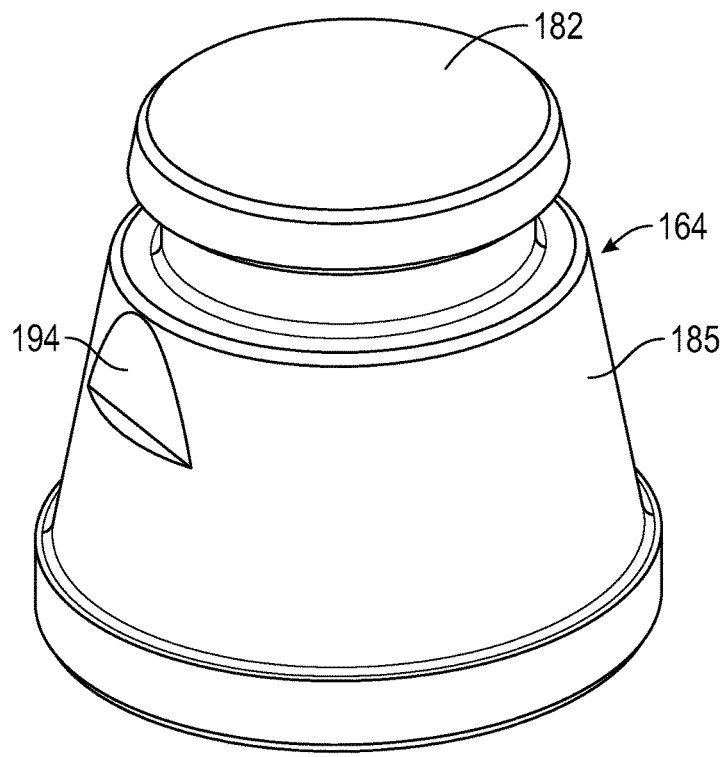
FIG. 34 is an enlarged side perspective view of the denture attachment housing of FIG. 33, illustrating an anti-rotation flat in the outer surface.

Denture cap or attachment housing 164 has an end wall 182 and an annular skirt 184 extending from end wall 182. Housing 164 has a generally tapered outer surface 185, as best seen in FIGS. 32 and 34. The inner surface of skirt 184 defines a cavity 186 having concave inner surface portion 187 configured for engagement with the convex outer surface 167 of abutment 162 in the mated condition of the parts (see FIG. 32). In this embodiment, a threaded bore 188 extends inwards from the inner end of cavity 186 and terminates in end wall 182, unlike the embodiment of FIGS. 1 to 6C where the threaded bore 111 extends through the cap end wall and is open at both ends. The cavity 183 has an annular indent 189 between concave surface portion 187 and threaded bore 188 which defines stop surface 190 having a similar function to stop surface 127 of FIG. 1. Outer surface 185 has an outer groove 192 adjacent the outer or upper end face, which provides a mechanical feature or indent for adhesive, and an annular rim 193 at its inner or lower end. An anti-rotation flat 194 is provided on the outer tapered surface of the housing (see FIG. 34).

Retention member 165 has a flexible shaft or neck 195 and a generally part-spherical or convex head or ball 196 at the end of neck 195 for snap engagement in the socket of abutment 162, as described in more detail below. Lead-in end 197 of the spherical surface engages tapered entrance opening 174 of the abutment socket to help guide the head into the socket. Shaft or neck 195 has a threaded end portion 199 configured for threaded engagement in threaded bore 188 of cap 164, and an annular flange 200. The closed outer end of the threaded bore in this embodiment prevents adhesive from entering the bore and bonding to the retention member during assembly. As in the first embodiment, head 196 has a flat outer end face 191 with a hex indent 198 for engagement with an insertion tool for tightening threaded shaft portion 199 into matching threaded bore 188 of cap 164 until annular flange 200 engages stop face 190 at the inner end of annular portion 189 of cavity 186. The portion of the neck or shaft 195 between annular flange 200 and head 196 is thin enough to deflect to accommodate engagement of the head portion in an offset abutment, in the same manner as described above in connection with FIGS. 6A to 6C illustrating the offset attachment of the retention member in the abutment of the first embodiment. In one embodiment, the material used in manufacture of the retention member and the neck dimensions are selected to permit insertion of the head portion in abutments with offsets of up to twenty degrees or up to thirty degrees with low or minimal risk of breaking.

In one embodiment, retention member 165 is formed from a compressible or elastomeric material as in the previous embodiments, such as a polymer or a soft metal, non-limiting examples of which include polymers such as polyether ether ketone (PEEK) or polyoxymethylene or acetal polymers such as Delrin®, and soft metals such as nickel titanium (nitinol), pink TiCN (titanium carbo nitride) or titanium. The soft metal may be a coating on the surface of the head portion in some embodiments. In one embodiment, the surfaces may be coated with a gold nitride coating to reduce friction.

The frictional snap-fit engagement of the ball or head 196 in the socket of retention member 165 is similar to that described above in connection with the first embodiment. FIG. 32 illustrates the head 196 fully engaged in socket in the case of an aligned abutment. The maximum convex diameter of head 196 is slightly greater than that of the inward projection 178, so that the compressible material of the head is compressed slightly as the head 196 is forced into the socket. Once the head is frictionally snap-fit into the socket in the position illustrated in FIG. 32, the sharp edge or barb 180 bites into the ball to resist removal, similar to an arrow head, as best seen in the enlarged view of FIG. 33. This annular detent or sharpened feature in the abutment grabs the ball or head 196 for a 360 degree engagement of the ball regardless of the angle of insertion. Because retention member 165 is made of a compressible polymer or soft metal material, neck or shaft 195 is also capable of flexing in the case of engagement with an offset abutment, as described above. The barb feature or sharpened edge concentrates the compressive load on a smaller area of the ball or head portion, created adding compression and friction and thus increasing retention force. This engagement results in material being sheared away from head 196 during prosthesis removal by a dental professional, requiring the retention members of removed prostheses to be replaced. This increases retention consistency. The barb produces little or no increase in the required insertion force, but increases the retention force opposing removal from the abutment.

As illustrated in FIG. 32, there is a significant clearance between head 196 of the retention member and socket 168 of abutment in the attached condition, and the head portion contacts the socket only at annular projection or barb 178, 180, as seen in FIG. 33. The socket provides increased clearance for offset attachment as compared to the first embodiment where the end of the head 112 is close to the threaded portion of the abutment when attached as illustrated in FIG. 5.

In one embodiment, a set of retention members which have different amounts of retention force may be provided, and the different members may be color coded for ease of initial selection of a retention member with a desired retention force at each anchor position of a prosthesis, as well as ease of replacement when needed. When replacing a retention member, original function may be maintained by replacing each removed retention member with a corresponding retention member of the same color. A clinician may use a mix of retention forces at different locations in an appliance due to specific conditions, for example for opposing cantilever forces. Retention forces may be varied in different ways, such as providing retention members of different diameters and/or materials, and by providing flats of different sizes. The greater the diameter, the higher the retentive force, since the inward projection cuts further into the head when fully engaged. A smaller diameter head provides less retentive force. Retention force may also be varied by using different, softer or harder compressible materials for head. The retention force may vary from anywhere between about 10 to about 75 pounds, although some embodiments may provide as little as about 1 pound of retention force for use in the initial positioning of the dental appliance and dental anchoring assembly.

Figure 35A:
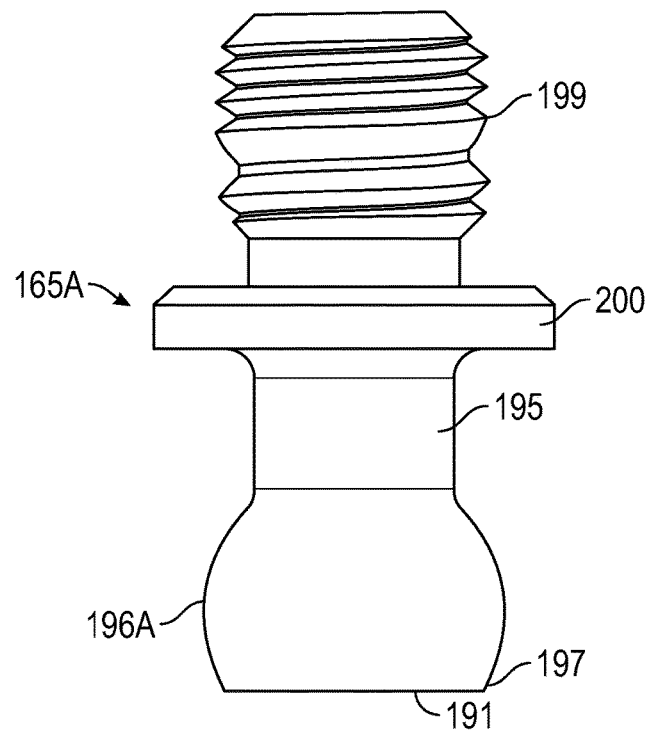
FIGS. 35A to 35C are side elevation views of a plurality of retention members with balls or heads of varying materials or configuration for providing different amounts of retention force.
Figure 35B:
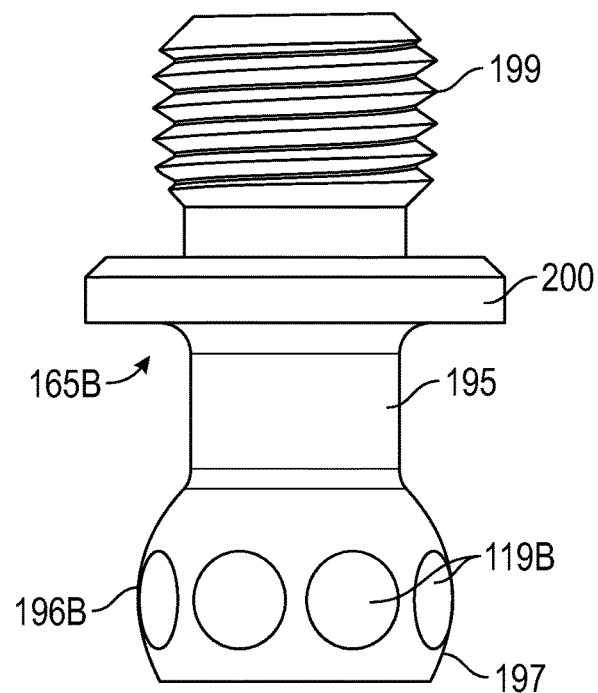
Figure 35C:
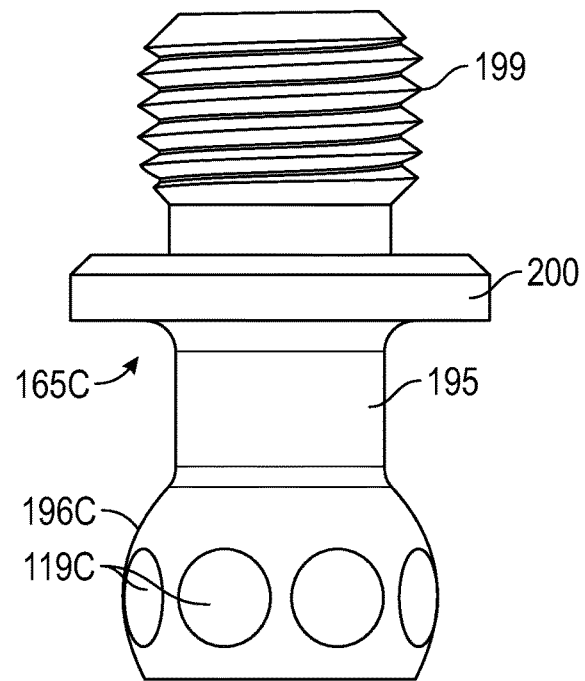

FIGS. 35A-35C illustrate examples of color coded retention members providing different retention forces. In one embodiment, a set of four color coded retention members may be provided as follows:

1. High retention force—Retention member 165A of FIG. 35A
2. Medium retention force—Retention member 165B of FIG. 35B
3. Low retention force—Retention member 165C of FIG. 35C
4. Lowest retention force—Processing member or ball which is identical in shape and dimensions to retention member 165C but is of a more compliant material. These retention members may be color coded according to any selected color scheme, for example in one embodiment, retention member 165A may be green, retention member 165B may be tan, retention member 165C may be blue, and the processing member may be black to correspond to the color of a commonly used Locator Processing Insert. The desired color may be provided by a suitable surface coating or by color of the material used for making the retention member. Color coding of the retention member helps to ensure replacement retention members keep the original function by providing the same or substantially the same retention force as the replaced retention or ball member. A dental appliance may have different retention members secured in the denture attachment housings or caps, depending on the varying amounts of retention or removal force required at different locations. Thus, with this assembly, there will be retention members of different colors, which can each be replaced with a retention member of the appropriate color when needed.

Removal force may be controlled by ball diameter, flats, and the softness of the material. The set of retention members of FIGS. 35A to 35C are identical apart from their different colors and the outer surface of the part-spherical head which is modified to provide varying retention or removal forces, and like reference numbers are used for like parts as appropriate. All of the retention members 165A, 165B and 165C in this embodiment are made of the same material, and in one aspect they are made from a polymer material such as polyether ether ketone (PEEK), while the processing ball or retention member (not illustrated) is made of a softer material such as an acetone polymer, e.g. Delrin®, and is of shape and dimensions matching retention member 165C of FIG. 35C. The outer convex or part spherical surface of the head 196A of member 165A of FIG. 35A is completely smooth, while the external ball-shaped or convex curved surfaces of the heads 196B and 196C of retention members 165B and 165C of FIGS. 35B and 35C, respectively, have a series of flats or flattened portions 119B and 119C around the circumference of surface to reduce the amount of friction between the curved surface of the head and the corresponding projection 120 of the socket, as described above in connection with FIGS. 2 and 3. Flats 119C are larger and slightly deeper than flats 119B, so that the retention or removal force of ball or retention member 165B is higher than that of the retention member 165C. Since no flats are provided on head 196 of FIG. 35A and the head has a smooth outer convex surface, the amount of friction between head 196 and projection 178 is higher, and the projection digs more deeply into the compressible surface of the head than in the retention members of FIGS. 35B and 35C which have substantially the same maximum diameter as head 196A apart from the flats. Heads of different dimensions and materials may be provided for varying frictional forces.

The insertion technique is similar or identical to that described above in connection with the first embodiment. The neck or stem diameter is designed to allow the retention member to be inserted into a divergent implant with minimal risk of breaking. In one embodiment, the stem allows insertion at up to a thirty degree angle (as described above in connection with FIGS. 6A to 6C). The shape of the head or ball of the retention member along with the lead-in end 197 of the part-spherical surface allows for typical implant divergence.

Figure 36:
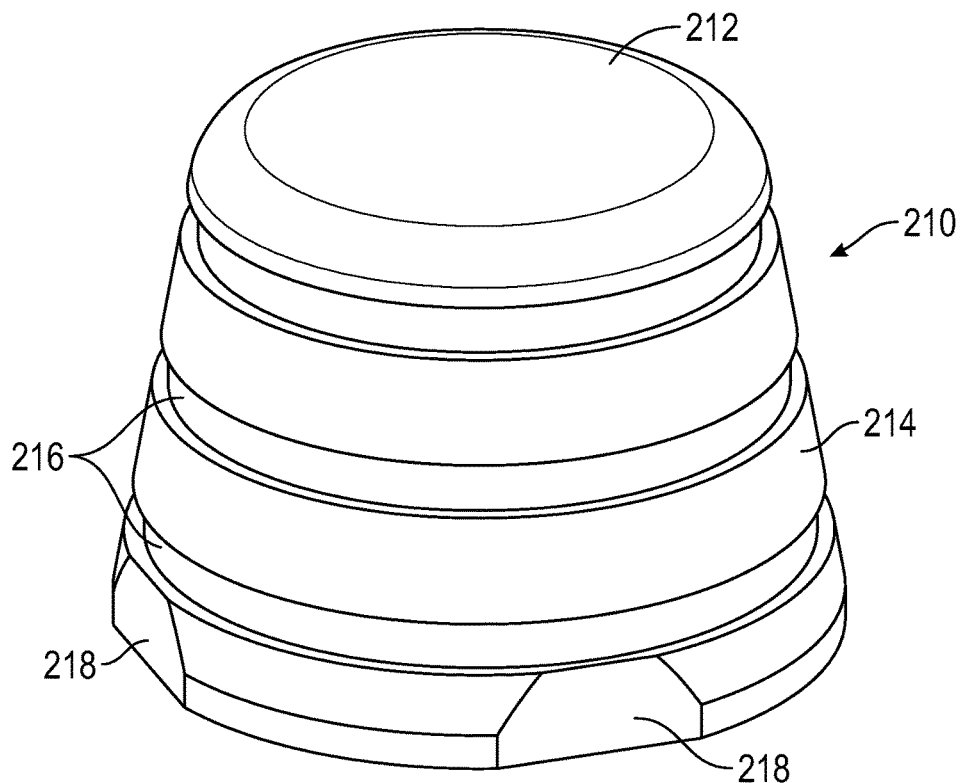
FIG. 36 is an enlarged side perspective view of one embodiment of a processing cap for forming a processing cap cavity in a dental appliance suitable for bonding to the denture attachment housing of FIGS. 31 to 33.
Figure 37:
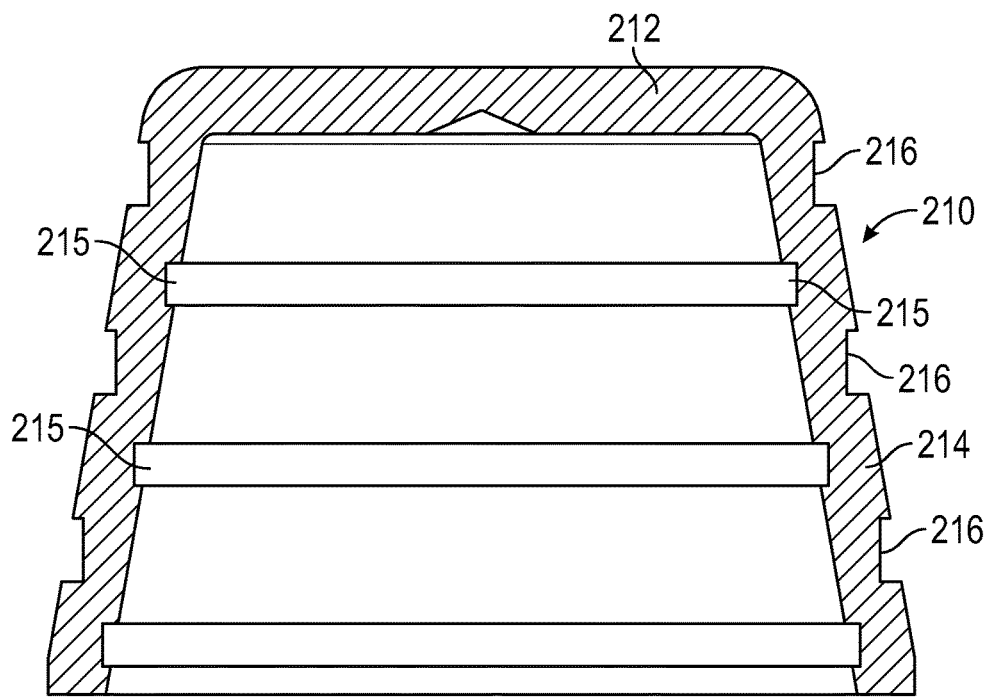
FIG. 37 is a cross-sectional view of the processing cap of FIG. 36.

FIGS. 36 and 37 illustrate an embodiment of a processing cap 210 for use with the denture attachment assembly of FIGS. 31 to 35C. This part is designed to be fabricated or formed into an all acrylic prosthesis, and provides the position and depth of a pocket into which the dental attachment housing is subsequently bonded. FIG. 38 illustrates cap 210 with the denture attachment housing 164 on an abutment 162. Cap 210 has an end wall 212 and a tapered annular wall or skirt 214 extending from end wall 212. The taper of wall 214 matches that of wall 185 of denture attachment housing (DAH) 164 and provides a lead-in for more precise guided bonding to the DAH. Wall 214 has inner grooves 215 for adhesive to improve bonding of DAH 164 into the cap and outer grooves 216 which provide indents or features for receiving acrylic. A series of flats 218 around the lower end of outer surface 214 provide some degree of resistance to rotation forces experienced during installation of retention members 165 or processing members. In one embodiment, both the denture attachment housing and processing cap are anodized pink.

FIGS. 39 and 40 illustrate one embodiment of an abutment analog 220 for use during model fabrication, while FIG. 41 illustrates dental attachment housing 164 and processing cap 210 secured to abutment analog 220 with retention ball or member 165. As illustrated in FIGS. 39 and 40, abutment analog 220 has a head portion 221 and a downwardly depending shaft 222, and an inlet opening 223 in the upper end of head portion 221 leading into socket 224. The head portion has a generally cylindrical outer surface with a step in diameter forming a shoulder 225 below the upper end of analog 220. As seen in FIG. 41, shoulder 225 engages the lower end of DAH 164 on attachment to the analog to restrict or prevent tipping or tilting of the DAH during model fabrication.

Figures 43, 44:
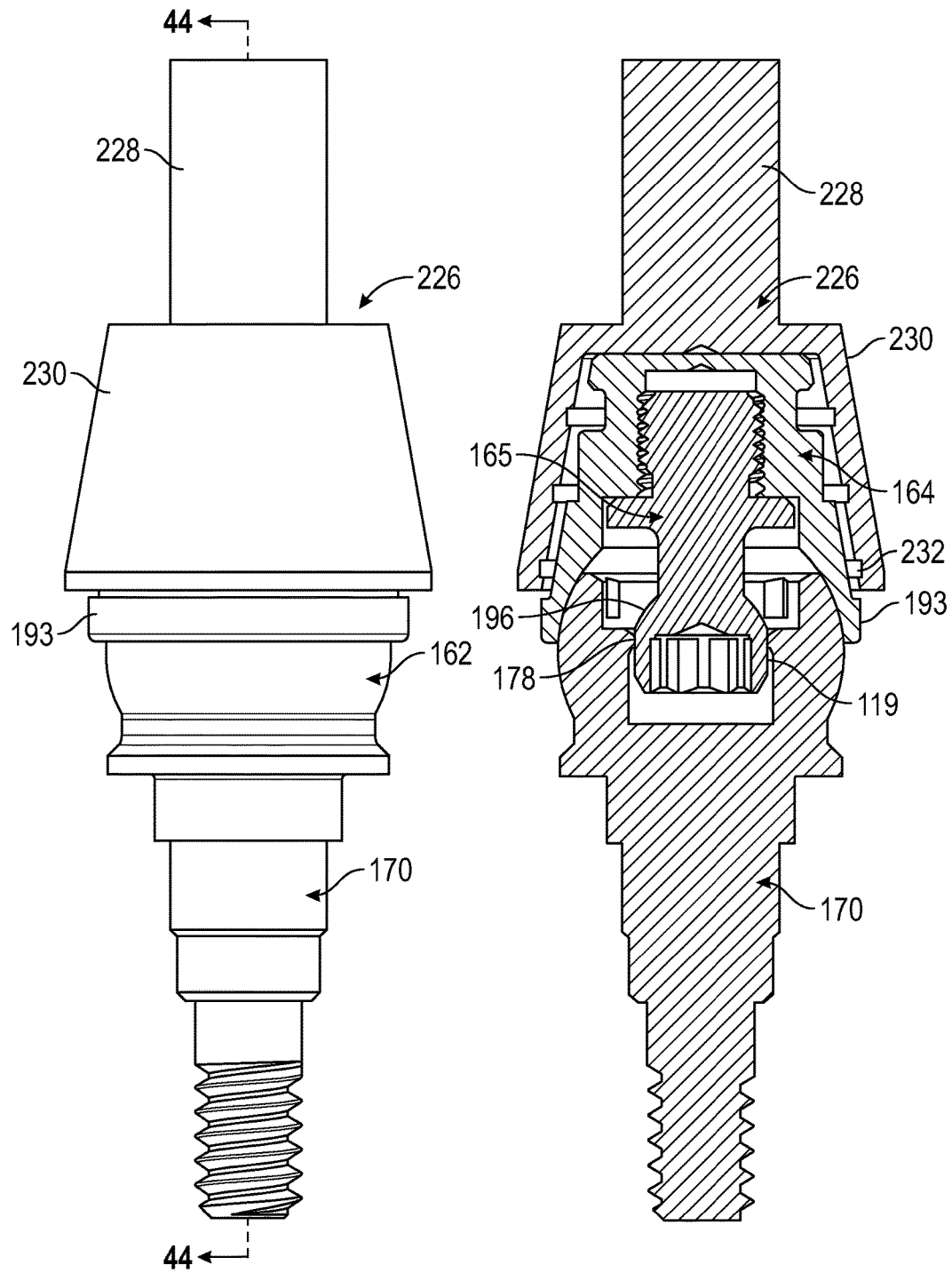
FIG. 43 is a side perspective view of the dental attachment assembly of FIGS. 31 to 34 with the waxing cap of FIG. 42 engaged over the denture attachment housing.
FIG. 44 is a cross-sectional view of the assembly and waxing cap on the lines 44-44 of FIG. 43.

FIG. 42 illustrates a waxing cap 226 used for prosthesis wax-up in order to make a recess in the cast framework for binding the DAH 164 in place. Waxing cap has a shaft 228 and a hollow, tapered head portion 230 matching the taper of processing cap 210 and a cavity 231 matching the cavity in processing cap 210 with a similar set of internal grooves 232 on the inner surface of the cavity. FIGS. 43 and 44 illustrate waxing cap 226 secured over a denture attachment housing or DAH 164 secured to abutment 162 by retention member 165.

Figure 45:
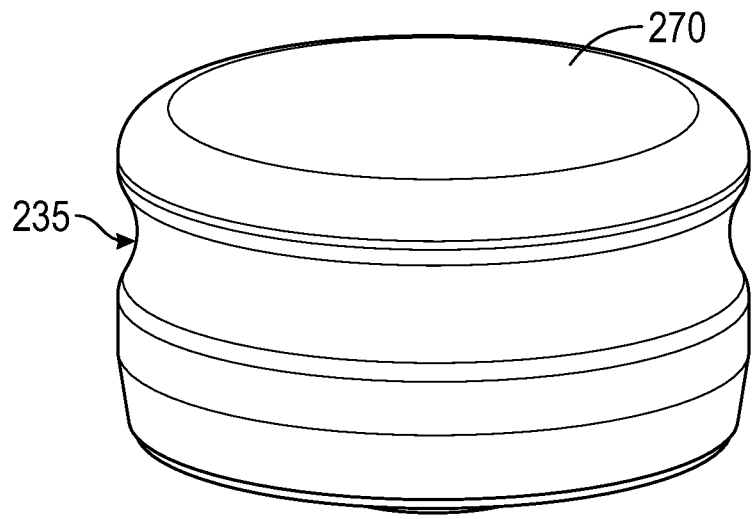
FIG. 45 is a top side perspective view of a snap-on healing cap for covering up the opening in the abutment of FIGS. 31 to 33 during the healing phase.
Figure 46:
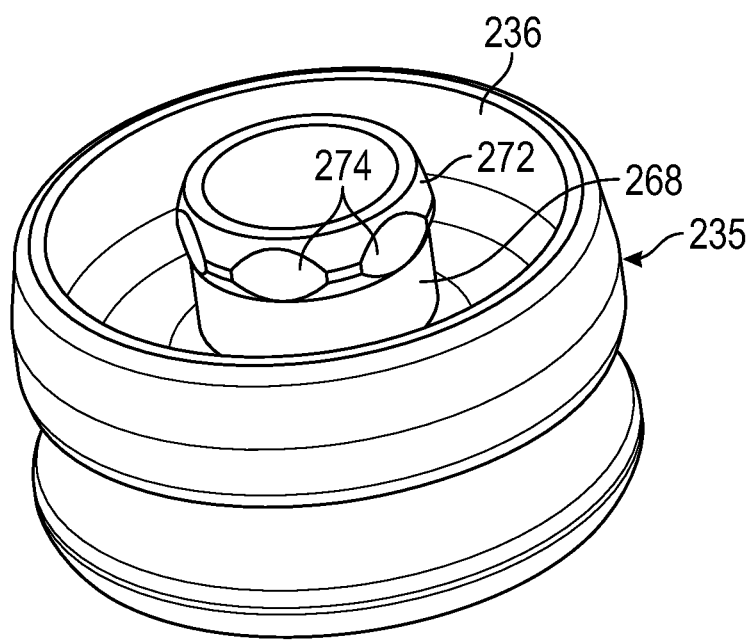
FIG. 46 is a bottom perspective view of the healing cap of FIG. 45, illustrating the retention head analog.
Figure 47:
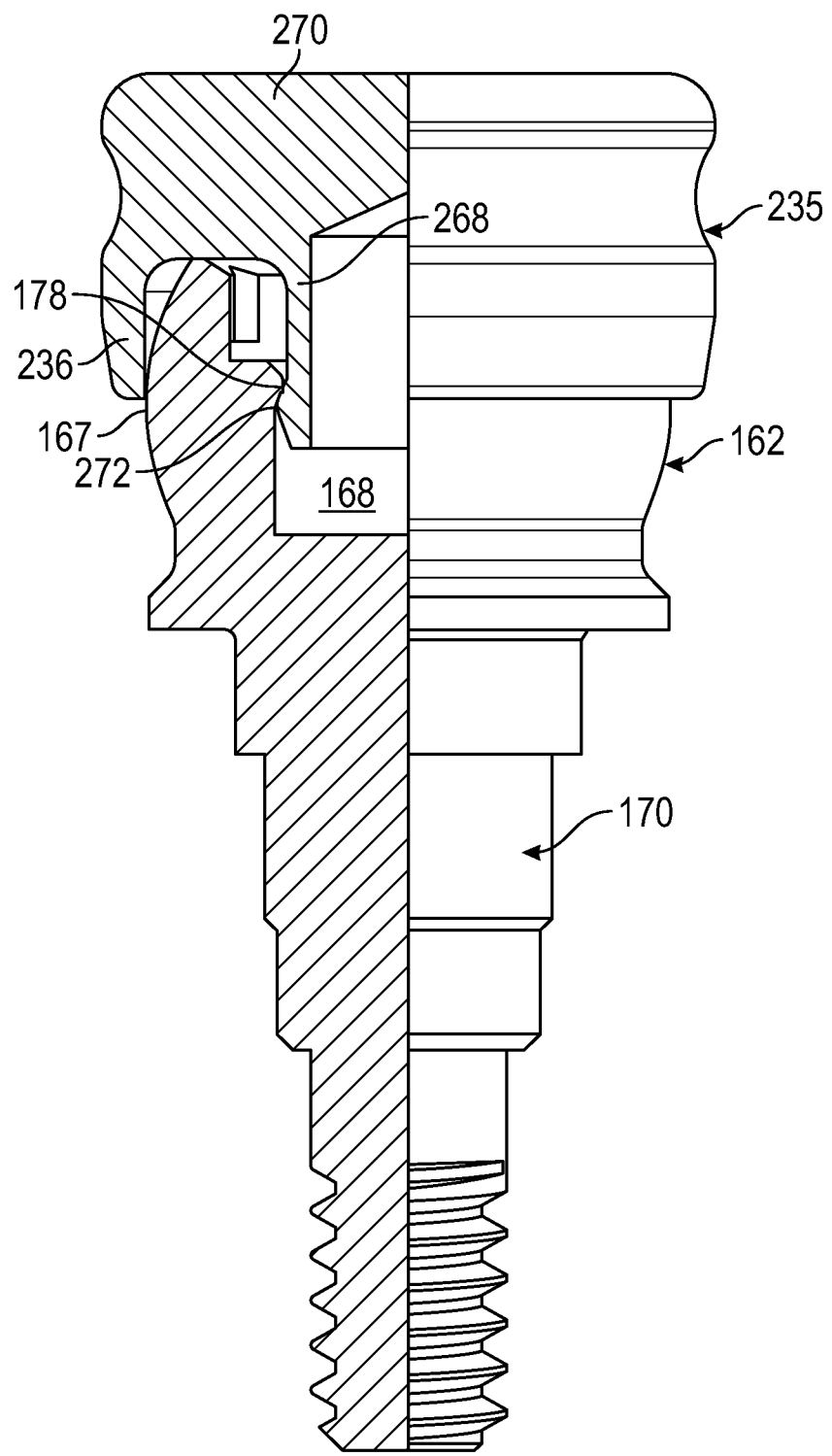
FIG. 47 is partially sectioned front elevation view of the healing cap of FIGS. 45 and 46 secured to the abutment of FIGS. 31 to 33.

FIGS. 45 and 46 illustrate a snap-on healing cap 235 to cover up the opening of socket 168 of abutment 162 during the healing. Healing cap 235 is different from prior healing caps designed to screw into the internal threads of abutments such as abutment 102 of the first embodiment. These internal threads are eliminated in the abutment 162 of this embodiment, as described above in connection with FIGS. 31 to 33. Instead of internal threads, healing cap 235 has an outer wall 236 designed to engage over the outer surface 167 of abutment 162 and a stem 268 extending from upper wall 270 of cap 235 which has an enlarged end portion 272 designed for frictional snap engagement with annular projection or barb 178 in abutment socket 168 in a similar manner to the head 196 of retention member 165, as illustrated in FIG. 47. Head or end portion 272 has a convex annular portion having spaced flats 274 around its outer surface, in a similar manner to the heads of retention members 165B and 165C of FIGS. 35B and 35C.

Figure 48:
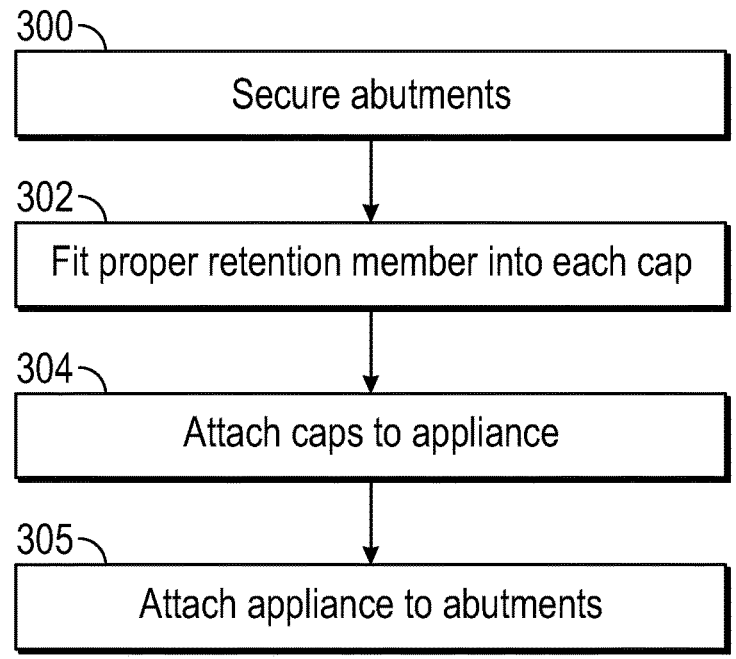
FIGS. 48 and 49 are flow diagrams illustrating methods of attaching a dental appliance with at least one dental attachment assembly in the lab or in a patient's mouth, respectively.
Figure 49:
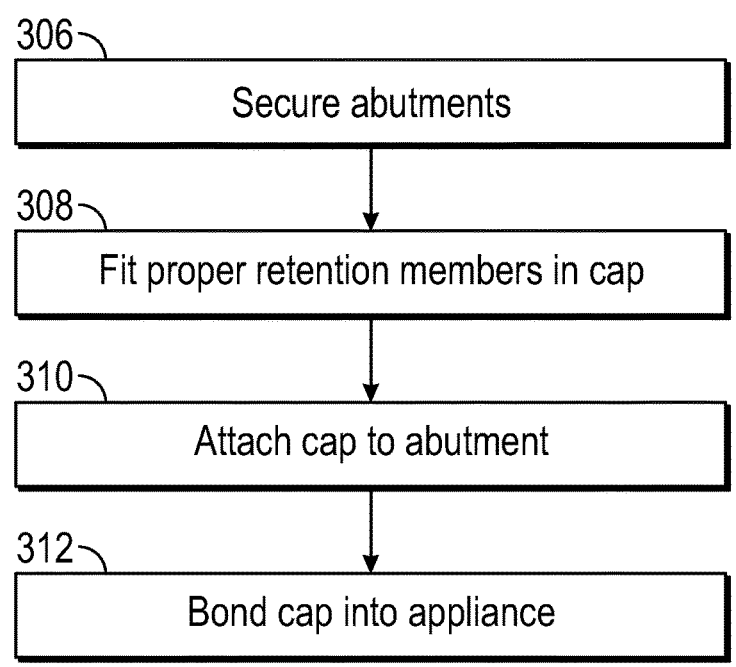

FIG. 48 illustrates one embodiment of a method of attaching a dental appliance to a plurality of implants in the lab using any of the dental attachment assemblies described above. In a first step 300, abutments are secured to implants or other structures in a model. Next, the proper retention members are fitted into each cap (step 302), and the caps are attached to the denture or appliance (step 304). Finally, the appliance is attached to the respective abutments using the frictionally retained retention members (step 305). FIG. 49 illustrates an embodiment of an alternative, in-mouth pick up method for securing an appliance in a patient's mouth. In this case, the abutments are secured to implants or other structure at the selected locations in the patient's mouth (step 306). Selected retention members of appropriate retention forces are then fitted into the respective caps in the appliance (step 308). The caps are then secured to the respective abutments via the frictionally engaged retention members (step 310). Finally, the caps are bonded into the appliance (step 312).

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A dental attachment assembly, comprising:
   a denture attachment housing for securing with a dental appliance, the denture attachment housing having an inner cavity having an inner end wall and an open outer end;
   an abutment for securing to a dental base structure, the abutment having a central longitudinal axis, a first end and a second end, and a socket having an outer end opening at the first end of the abutment and an inner end, and extending inward from the outer end opening towards the second end of the abutment, the socket having a continuous peripheral wall extending from the outer end opening to the inner end, and an annular projection in the peripheral wall and axially spaced from the outer end opening, the annular projection having a rounded portion with an undercut edge forming a barb; and
   a retention member having a first end secured to the inner end wall of the inner cavity, an at least partially spherical head at a second end of the retention member for insertion in the socket, and a shaft extending from the first end to the head, the head having a first end at a junction between the head and the shaft, a second end, and a maximum diameter surface portion spaced from the first end, the maximum diameter surface portion being configured for frictional, detachable engagement with the annular projection in the socket at a location which is axially spaced from the junction with the shaft and the outer end opening of the socket when the head is engaged in the socket, at least the maximum diameter surface portion of the head being formed of a compressible material whereby the annular, inwardly directed projection compresses an opposing surface portion of the head and the barb bites into the material of the head to resist removal of the head from the socket.

2. The assembly of claim 1, wherein the head engages only the annular projection and not any other part of the socket when fully inserted in the socket.

3. The assembly of claim 1, wherein the entire retention member is formed of a compressible material.

4. The assembly of claim 3, further comprising a set of retention members having heads configured to provide different amounts of retention force.

5. The assembly of claim 4, wherein each retention member is made of a compressible material selected from the group consisting of polymers and metals.

6. The assembly of claim 5, wherein at least one retention member is made of a different material which is softer than the other retention members in the set.

7. The assembly of claim 4, wherein the barb has an inner diameter and the heads are at least partially spherical and have a maximum diameter greater than the inner diameter of the barb, the maximum diameter surface portion of at least a first retention member is a smooth, uninterrupted convex outer surface and one or more other retention members in the set have a maximum diameter surface portion which has a series of spaced flattened portions configured to provide a reduced retention force relative to the first retention member when the maximum diameter outer surface portion engages the barb.

8. The assembly of claim 4, wherein the heads are of different colors corresponding to different amounts of retention force.

* * * * *